United States Patent
Karthikeyan et al.

(10) Patent No.: US 10,463,760 B2
(45) Date of Patent: Nov. 5, 2019

(54) ABSORBENT, BREATHABLE AND PATHOGEN BLOCKING/KILLING WOUND CARE DRESSING AND FABRICATION THEREOF

(71) Applicant: InMEDBio, LLC, Oshkosh, WI (US)

(72) Inventors: Ashwinraj Karthikeyan, Oshkosh, WI (US); Annamalai Karthikeyan, Oshkosh, WI (US)

(73) Assignee: InMEDBio, LLC, Oshkosh, WI (US)

(*) Notice: Subject to any disclaimer, the term of this patent is extended or adjusted under 35 U.S.C. 154(b) by 0 days.

(21) Appl. No.: 16/177,416

(22) Filed: Oct. 31, 2018

(65) Prior Publication Data
US 2019/0125924 A1     May 2, 2019

Related U.S. Application Data

(60) Provisional application No. 62/579,588, filed on Oct. 31, 2017.

(51) Int. Cl.
     *A61L 15/46*      (2006.01)
     *A61L 15/42*      (2006.01)
     (Continued)

(52) U.S. Cl.
     CPC ...... *A61L 15/425* (2013.01); *A61F 13/00029* (2013.01); *A61F 13/00034* (2013.01);
     (Continued)

(58) Field of Classification Search
     CPC ...... A61L 15/425; A61L 15/18; A61L 15/225; A61L 15/44; A61L 2300/404;
     (Continued)

(56) References Cited

U.S. PATENT DOCUMENTS

| | | |
|---|---|---|
| 4,715,857 A | 12/1987 | Juhasz et al. |
| 4,817,594 A | 4/1989 | Juhasz |

(Continued)

FOREIGN PATENT DOCUMENTS

| | | |
|---|---|---|
| CN | 1202379 A | 12/1998 |
| EP | 0106439 B1 | 11/1987 |

(Continued)

OTHER PUBLICATIONS

PCT Written Opinion and Search Report for PCT/US18/58591.

*Primary Examiner* — Kai H Weng
(74) *Attorney, Agent, or Firm* — Woods Rogers PLC; Nathan A. Evans

(57) ABSTRACT

This invention relates to a multi-layer wound site dressing specifically designed to treat chronic wounds and simultaneously block external pathogens from infecting the wound site from the environment. The said wound dressing comprises five layers; each layer performs a specific functionality in healing and protecting the wound site. The said layers of wound care dressing comprise (i) a permeable non-adherent woven or non-woven membrane in contact with wound site, (ii) a nanofibrous composite layer made of superabsorbent, activated carbon and a polymer (iii) a hydrophobic insulating membrane which is permeable to air with an adhesive edge, (iv) a nanofibrous membrane made of polymer and activated carbon hosting functional germicidal ions, and (v) an air permeable non-woven membrane with adhesive edge. The said layers are compounded by pressing and coating to make a comprehensive multi-layer wound care dressing product.

23 Claims, 20 Drawing Sheets

(51) Int. Cl.
   *A61L 15/44* (2006.01)
   *A61L 15/18* (2006.01)
   *A61L 15/22* (2006.01)
   *A61F 13/00* (2006.01)
   *A61F 13/20* (2006.01)
   *A61F 13/02* (2006.01)

(52) U.S. Cl.
   CPC .. *A61F 13/00063* (2013.01); *A61F 13/00068* (2013.01); *A61F 13/0206* (2013.01); *A61F 13/0243* (2013.01); *A61F 13/2074* (2013.01); *A61L 15/18* (2013.01); *A61L 15/225* (2013.01); *A61L 15/44* (2013.01); *A61L 2300/404* (2013.01)

(58) Field of Classification Search
   CPC .......... A61F 13/00029; A61F 13/00034; A61F 13/00063; A61F 13/00068; A61F 13/2074
   See application file for complete search history.

(56) References Cited

U.S. PATENT DOCUMENTS

| | | |
|---|---|---|
| 6,399,091 B1 | 6/2002 | Berthold et al. |
| 6,592,888 B1 | 7/2003 | Jensen et al. |
| 7,462,753 B2 | 12/2008 | Ma et al. |
| 7,759,537 B2 | 7/2010 | Bishop et al. |
| 7,759,539 B2 | 7/2010 | Shaw et al. |
| 7,803,980 B2 | 9/2010 | Griffiths et al. |
| 8,124,826 B2 | 2/2012 | Addison et al. |
| 8,257,778 B2 | 9/2012 | Larsen et al. |
| 8,563,447 B2 | 10/2013 | Canada et al. |
| 8,637,072 B2 | 1/2014 | Kershaw et al. |
| 8,728,513 B2 | 5/2014 | Woods |
| 8,779,230 B2 | 7/2014 | Murphy et al. |
| 9,000,252 B2 | 4/2015 | Bradford et al. |
| 9,125,963 B2 | 9/2015 | Ko et al. |
| 9,132,040 B2 | 9/2015 | Van Holten et al. |
| 9,295,749 B2 | 3/2016 | Addison et al. |
| 9,510,977 B2 | 12/2016 | Ko et al. |
| 2005/0182347 A1 | 8/2005 | Bishop et al. |
| 2008/0032934 A1 | 2/2008 | Ellis-Behnke et al. |
| 2008/0125617 A1 | 5/2008 | Puchek |
| 2009/0047332 A1 | 2/2009 | Kim et al. |
| 2010/0030170 A1 | 2/2010 | Keller et al. |
| 2013/0053807 A1 | 2/2013 | Taylor et al. |
| 2013/0112077 A1 | 5/2013 | Rosati |
| 2013/0296818 A1 | 11/2013 | Bradford et al. |
| 2014/0283851 A1 | 9/2014 | Dowson et al. |
| 2017/0100504 A1 | 4/2017 | Taylor et al. |

FOREIGN PATENT DOCUMENTS

| | | |
|---|---|---|
| EP | 1314410 B1 | 2/2010 |
| GB | 2531344 A | 4/2016 |

| Dressing | Equation | Change (g/min) | R^2 | | Conclusion |
|---|---|---|---|---|---|
| Areza Algiante | y = -0.0896x + 68.702 | 0.0896 | $R^2$ | = 0.9984 | Highly Breathable |
| 3m Tegaderm | y = -0.0049x + 68.808 | ~0 | $R^2$ | = 0.8126 | Not Breathable |
| Primapore | y = -0.0288x + 69.282 | 0.0288 | $R^2$ | = 0.9665 | Low Breathability |
| Duoderm | y = -0.0018x + 75.348 | ~0 | $R^2$ | = 0.5328 | Not Breathable |
| Kendall curity non-adhering dressing | y = -0.0438x + 73.684 | 0.0438 | $R^2$ | = 0.9955 | Moderately Breathable |
| Covidien telfa | y = -0.0318x + 66.552 | 0.0318 | $R^2$ | = 0.9971 | Low Breathability |
| The invention | y = -0.0702x + 68.986 | 0.0702 | $R^2$ | = 0.9979 | Highly Breathable |
| Mass Control | y = -0.5193x + 67.038 | 0.5193 | $R^2$ | = 0.9958 | CONTROL |

Figure 18

| Iteration | Set thickness (mm) | Activated Carbon No. | Activated Carbon % total | Absorbent No. | Absorbent % total | Binder No. | Binder % total | Solvent No. | Solvent % by mixture % |
|---|---|---|---|---|---|---|---|---|---|
| 1 | 0.75 | 2 | 36.64% | 2 | 36.84% | 1 | 26.53% | 1 | 0.00% |
| 2 | 0.75 | 2 | 36.92% | 2 | 36.59% | 1 | 26.49% | 1 | 0.00% |
| 3 | 0.75 | 3 | 38.34% | 3 | 35.14% | 1 | 26.52% | 1 | 97.38% |
| 4 | 0.50 | 4 | 41.57% | 4 | 37.41% | 1 | 21.01% | 1 | 69.59% |
| 5 | 0.40 | 4 | 42.29% | 4 | 38.10% | 1 | 19.61% | 1 | 53.37% |
| 6 | 0.75 | 4 | 47.58% | 4 | 42.76% | 2 | 9.66% | 2 | 119.16% |
| 7 | 0.47 | 4 | 47.58% | 4 | 42.76% | 2 | 9.66% | 2 | 119.16% |
| 8 | 0.50 | 4 | 47.58% | 4 | 42.76% | 2 | 9.66% | 2 | 119.16% |
| 9 | 0.47 | 5 | 39.95% | 4 | 36.08% | 1 | 23.97% | 1 | 48.90% |
| 10 | 0.50 | 5 | 39.95% | 4 | 36.08% | 1 | 23.97% | 1 | 48.90% |
| 11 | 0.47 | 5 | 50.04% | 4 | 44.91% | 2 | 5.05% | 2 | 109.52% |
| 12 | 0.47 | 5 | 50.04% | 4 | 44.91% | 2 | 5.05% | 2 | 109.52% |
| 13 | 0.47 | 4 | 47.58% | 4 | 42.76% | 2 | 9.66% | 2 | 119.16% |
| 14 | 0.50 | 4 | 47.58% | 4 | 42.76% | 2 | 9.66% | 2 | 119.16% |

Percentage of Activated Carbon, absorbent, and binder total 100%
Solvent % is based on the percent of the mixture to solvent. (ex. 5 g of total mixture, and 10g solvent, is 200%)
Set thickness is the coat height

Activated Carbon

| No. | Name | Iodine No. (mg/g) | Mesh | Unifromity |
|---|---|---|---|---|
| 2 | CN9-A2 | | UnMeshed | Semi-Uniform |
| 3 | C12-A2 LC - N1 to | | UnMeshed | Semi-Uniform |
| 4 | N6 LC - N1 to | 1119 | 200 | Uniform |
| 5 | N6 | 1119 | 325 | Uniform |

Absorbent

| No. | Name | Mesh |
|---|---|---|
| 2 | MediSAP 715 | 50+ |
| 3 | PA001 | 50+ |
| 4 | LiquiBloc k 2G-120 | 100 |

Figure 19

| Iteration | Set thickness (mm) | Activated Carbon No. | Activated Carbon % total | Absorbent No. | Absorbent % total | Binder No. | Binder % total | Solvent No. | Solvent % by mixture % |
|---|---|---|---|---|---|---|---|---|---|
| 1 | 0.75 | 2 | 36.64% | 2 | 36.84% | 1 | 26.53% | 1 | 0.00% |
| 2 | 0.75 | 2 | 36.92% | 2 | 36.59% | 1 | 26.49% | 1 | 0.00% |
| 3 | 0.75 | 3 | 38.34% | 3 | 35.14% | 1 | 26.52% | 1 | 97.38% |
| 4 | 0.50 | 4 | 41.57% | 4 | 37.41% | 1 | 21.01% | 1 | 69.59% |
| 5 | 0.40 | 4 | 42.29% | 4 | 38.10% | 1 | 19.61% | 1 | 53.37% |
| 6 | 0.75 | 4 | 47.58% | 4 | 42.76% | 2 | 9.66% | 2 | 119.16% |
| 7 | 0.47 | 4 | 47.58% | 4 | 42.76% | 2 | 9.66% | 2 | 119.16% |
| 8 | 0.50 | 4 | 47.58% | 4 | 42.76% | 2 | 9.66% | 2 | 119.16% |
| 9 | 0.47 | 5 | 39.95% | 4 | 36.08% | 1 | 23.97% | 1 | 48.90% |
| 10 | 0.50 | 5 | 39.95% | 4 | 36.08% | 1 | 23.97% | 1 | 48.90% |
| 11 | 0.47 | 5 | 50.04% | 4 | 44.91% | 2 | 5.05% | 2 | 109.52% |
| 12 | 0.47 | 5 | 50.04% | 4 | 44.91% | 2 | 5.05% | 2 | 109.52% |
| 13 | 0.47 | 4 | 47.58% | 4 | 42.76% | 2 | 9.66% | 2 | 119.16% |
| 14 | 0.50 | 4 | 47.58% | 4 | 42.76% | 2 | 9.66% | 2 | 119.16% |

Percentage of Activated Carbon, absorbent, and binder total 100%
Solvent % is based on the percent of the mixture to solvent. (ex. 5 g of total mixture, and 10g solvent, is 200%)
Set thickness is the coat height

Activated Carbon

| No. | Name | Iodine No. (mg/g) | Mesh | Uniformity |
|---|---|---|---|---|
| 2 | CN9-A2 | | UnMeshed | Semi-Uniform |
| 3 | C12-A2 | | UnMeshed | Semi-Uniform |
| 4 | LC - N1 to N6 | 1119 | 200 | Uniform |
| 5 | LC - N1 to N6 | 1119 | 325 | Uniform |

Absorbent

| No. | Name | Mesh |
|---|---|---|
| 2 | MediSAP 715 | 50+ |
| 3 | PA001 | 50+ |
| 4 | LiquiBlock 2G-120 | 100 |

ABSORBENT, BREATHABLE AND PATHOGEN BLOCKING/KILLING WOUND CARE DRESSING AND FABRICATION THEREOF

CROSS-REFERENCE TO RELATED APPLICATIONS

This application relies on the disclosure of and claims priority to and the benefit of the filing date of U.S. Provisional Application No. 62/579,588 filed Oct. 31, 2017, the disclosure of which is hereby incorporated by reference in its entirety.

BACKGROUND

Field of the Invention

The invention relates to breathable, moisture retaining, pathogen preventing, super absorbent, and/or germicidal, wound dressings. These said multiple functionalities are due to a combination of component layers of this wound dressing with a seclusion blanket layer dedicated to pathogen blocking and to insulate active materials. In particular, it relates to a wound dressing for both acute and chronic wounds, which can be used to cover clean, contaminated, gangrenous, exuding, malodorous, and discharging wounds, and assist in their treatment. More specifically, it relates to wound dressings comprising of activated carbon, cellulose, superabsorbent polymers, such as sodium polyacrylate and its modifications; binders such as pliable silicone, and polyvinylidene fluoride; germicidal ions, such as ionic silver, and ionic copper; and macroporous or mesoporous membrane, such as non-woven polypropylene, HEPA membrane, ULPA membrane, woven and non-woven cotton, and non-glass based woven fiber cloth. Wound site treatment is further enhanced by a personalized layer and/or medication attributes when needed/prescribed.

Description of the Related Art

The invention is a safe, cost-effective, and comprehensive wound care dressing designed to prevent external infection and to accelerate the wound healing process of chronic wounds. Chronic wounds often require more than three months to heal, and may even linger for years due to repeated infections and complications.[3] Chronic wounds are most prevalent and dangerous to patients with conditions such as diabetes, obesity, or other immune system conditions.[1,6]

Current tactics to combat infection, in emerging markets especially, involve multiple products like dressings, gauze, with or without ointments that are both cumbersome and expensive. According to studies conducted of over 700 consumers, only 15.0% believed that current products were very absorptive, and only 16.8% believed current products were very effective at preventing infection. In the same study, 81.3% of consumers stated that it was important to kill pathogens attempting to enter a wound site, and 64.7% found that a wound healed better in a fully oxygenated environment. According to a study, the major problem consumers have with existing products is the lack of durability. More than 90% of consumers interviewed remarked that the dressings they usually use last less than a day, primarily due to lack of water resistance, absorptive capabilities, strength of the product, and adhesion to the skin. Using data from laboratory research, literature reviews (Chaby G., Senet P., Vaneau M., et al. 2007), and interviews with consumers, medical professionals, and wound care experts, it has been determined that the required solution for combating foot ulcers, specifically in emerging markets where current solutions are not addressing the problem needs, should integrate (what is referred to herein as) the "ABCs" of chronic wound healing: (A)ccelerate Healing, (B)lock Infection, and (C)omfort Wound(s).

Current products on the market and the prior art fail to address the critical "ABC" criteria. Further the products in the markets are priced prohibitively high for patients to pay out of pocket. Most of these products are not able to actively trap and kill external pathogens, and they rely on chemical agents with short lifespans that can have risky side effects.5 As for products that meet some of the established "ABC" criteria, they are large, expensive composite pads which are thick and limit airflow to the wound site; these pads do not debride the wound (actively break down dead tissue), often resulting in surgical procedures. For example, products using flexible silicone dressings are designed to conform to the body shape and color very well; however, the primary drawback is that these products provide minimal absorbance from wound site(s) and provide minimal or no air flow needed to heal the wounds. Wound care dressing made of hydrogels provides moisture stability; however, such a dressing is less suitable for chronic wounds in which exudates from chronic wounds are higher. Further, the evaporation of excess moisture is limited which creates higher risk for infections. Health care providers have to frequently monitor the wound site and change the dressing often to avoid contamination and to accelerate the treatment and healing. Consequently, service care providers need one product that resolves numerous issues, including the "ABC" issues.

Additionally, products in underserved and emerging markets revolve around very rudimentary treatment and care. In India, for example, the standard of care product, usually comprises using topical ointments, such as Mupirocin, and Betadine, as well as topical gels. These gels are on occasion mixed with collagen, and/or growth factors, and applied directly to the wound site. The wound is then covered with a thick cotton pad, or cotton pack. Afterwards it is thoroughly wrapped with gauzes, or saline gauzes, and tied together with crepe tape. This composition suffocates the wound, prevents a proper moist environment from forming, may cause allergic reactions, or interfere with the healing process, is not able to keep pathogens out, and is not costeffective.

Experiments were performed, as described below, to compare the current invention against over thirty-five current competitor products already on the market, found in both emerging and developed markets. Across metrics tested, the invention was found to be a preferred overall product for chronic wounds, according to the metrics determined most important, as shown herein. The invention scored higher in moisture control, breathability, exudate control, external pathogen prevention, toxicity, toxin control, inflammatory response, odor control, durability, and/or comfort when comparatively tested.

In the prior art products and procedures, no meaningful improvement has been made to prevent infections from the environment external of the wound site. The wound site is very vulnerable to infection from external contaminations, such as from various sources including pets, other people, contaminated places, etc. Such infections of a simple acute wound can result in chronic wounds that result in amputations and sometimes even in death. There is a need for an integrated wound care dressing product for acute and chronic wounds that is highly absorbent and breathable, while simultaneously blocking pathogens from external infections. In addition, a comprehensive wound care dressing procedure should incorporate a host of necessary features including odor control, water resistance, decreased inflammatory response, reduction of dead wound tissue, toxin control, durability, and comfort. Such multiple functionalities are incorporated in this present invention by dedicated component layers forming an integrated dressing product.

SUMMARY

In one aspect, the invention consists of a five-layer permeable membrane cloth. By one common but not limiting definition, permeable means a low or high deterrence to passive diffusion of atmospheric air and/or other things, such as gasses, through a membrane.

In a preferred embodiment, the current invention shields, traps, and kills pathogens attacking the wound site with a size-exclusion barrier. Lab tests as explained herein show that the activated carbon used in one aspect of this invention is microporous, such as with pore sizes less than 5 nm. These pores, according to one aspect of the invention, host functional germicidal ions. A web of nanofibrous polymer-carbon composite acts as physical barrier for larger allergens and captures smaller key pathogens, such as bacteria and viruses. Finally, in another aspect, moisture absorptive properties of a specialized absorption layer provide an oxygen rich environment which accelerates the healing process. The absorption layer also absorbs wound fluids and blood, prevents odors, and reduces the amount of pain from the wound.

A unique layering method for the product, with each layer performing multiple functions to minimize costs, is also taught herein. The inventive ability to exclude and kill pathogens on the pathogen-barrier side is unique, especially when considering a customer-oriented customization of the product. An insulating layer is provided for zonal isolation and to avoid potential toxic effects from the germicidal ion layer. Prior art wound healing devices, which do not have such barriers separating germicidal ions from the wound, increase the risk of the patient succumbing to argyria (a blue-gray discoloration of the human skin, eyes, internal organs, nails and gums); excessive doses can also cause possibly irreversible serious health problems, including kidney damage and neurological problems, such as seizures. Germicidal ions may also interact with medications such as penicillamine (Cuprimine, Depen), quinolone antibiotics, tetracycline, and thyroxine (Levothroid, Levoxyl, Synthroid). The current inventive dressing as taught herein is, in some aspects, enclosed within a thin insulating layer on each side of the carbon, preventing particulate matter from entering the dressing on one side, whilst allowing a healing environment on the wound side.

In one embodiment of the present invention, a product is provided comprising a biocompatible five-layer tailored laminate. This comprehensive dressing absorbs fluid waste, such as exudate (blood, plasma, etc.), and body waste, and provides a dedicated barrier layer while maintaining porosity throughout for air flow. This dressing is tailored for treating common types of chronic wounds such as venous stasis ulcers, arterial ulcers, and diabetic foot ulcers.6,8

The dressing technology of the invention comprises, but is not limited to, at least two embodiments with unique functionalities, namely healing and pathogen prevention. A first embodiment, namely healing, includes a permeable fabric layer that is in contact with the wound site along with, for example, a three-component composite membrane, comprising a superabsorbent polymer, microporous activated carbon, and a structural networking polymer. The composite membrane effectively removes all the exudates from a wound site, locks exudate within this membrane, and provides an oxygenated moist environment for treatment of the wound site, and accelerates healing of the wound.

The second embodiment, namely pathogen prevention, comprises a thin nanofibrous membrane made of polymer and activated carbon hosting functional germicidal ions. This layer is part of a dressing comprising, in one aspect, an air permeable woven or non-woven membrane with an adhesive edge. In one aspect, this dual layer barrier envelops the dual layer healing section of the dressing.

In one embodiment, the healing and preventing aspects are separated by an insulating layer which is permeable to air with an adhesive edge. The insulating layer is made of a hydrophobic non-woven polypropylene, HEPA membrane, and/or ULPA membrane, of the desired size, porosity and thickness. In one aspect, dual ring adhesion provides insulation from external wetting and internal wetting.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

FIG. 9 is a diagram showing results indicating that the invention is the preferred overall product across the metrics tested.

FIG. 11 is a diagram showing breathability testing where both the change and the R2 value were considered for a conclusion. A high change value and a linear (high R2 value) were desired for high breathability.

FIG. 18 is a chart showing test results.
FIG. 19 is a chart showing test results.

DETAILED DESCRIPTION OF THE INVENTION

Figure 1:
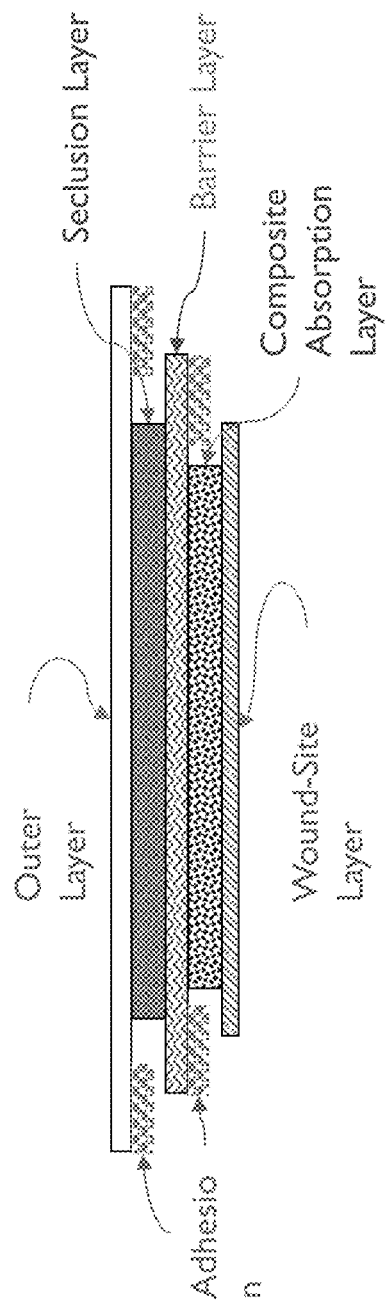
FIG. 1 is a schematic showing the side view of a 5-layer wound care dressing according to the present invention, including healing and preventing layers of the dressing separated by an insulating layer.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In the preferred embodiment, the invention comprises a biocompatible five-layer cloth. Going from the atmosphere to the wound site, in one aspect, the layers are: Macro-Porous Layer (5), which is designed to trap relatively larger pathogens, such as pollen, mold spores, and fungal spores; Micro-Porous/Germicidal Layer (4), which traps and kills relatively smaller pathogens, such as bacteria and viruses, via a size-exclusion barrier and germicidal ions; Ion-Barrier Layer (3), which is designed to keep harmful germicidal ions from entering the body and prevent seepage of exudate; Absorption Layer (2), which absorbs and retains exudate, de-toxifies the wound, and de-odorizes the wound; Wound-Site Layer (1), which regulates exudate flow, and maintains a non-adherence surface to the wound. In one aspect, the invention is breathable throughout.

Preferably, the invention is able to absorb amounts of fluid waste, while maintaining breathability throughout. In one aspect, the product is cost-effective, safely absorbs large amounts of exudate, and maintains a moist and oxygenated environment for accelerated healing, all while protecting the wound from external pathogens through both active and passive methods. FIGS. 1-6 show preferable features provided by the invention. Data supporting the ability to perform certain features are included herein.

Figure 4:
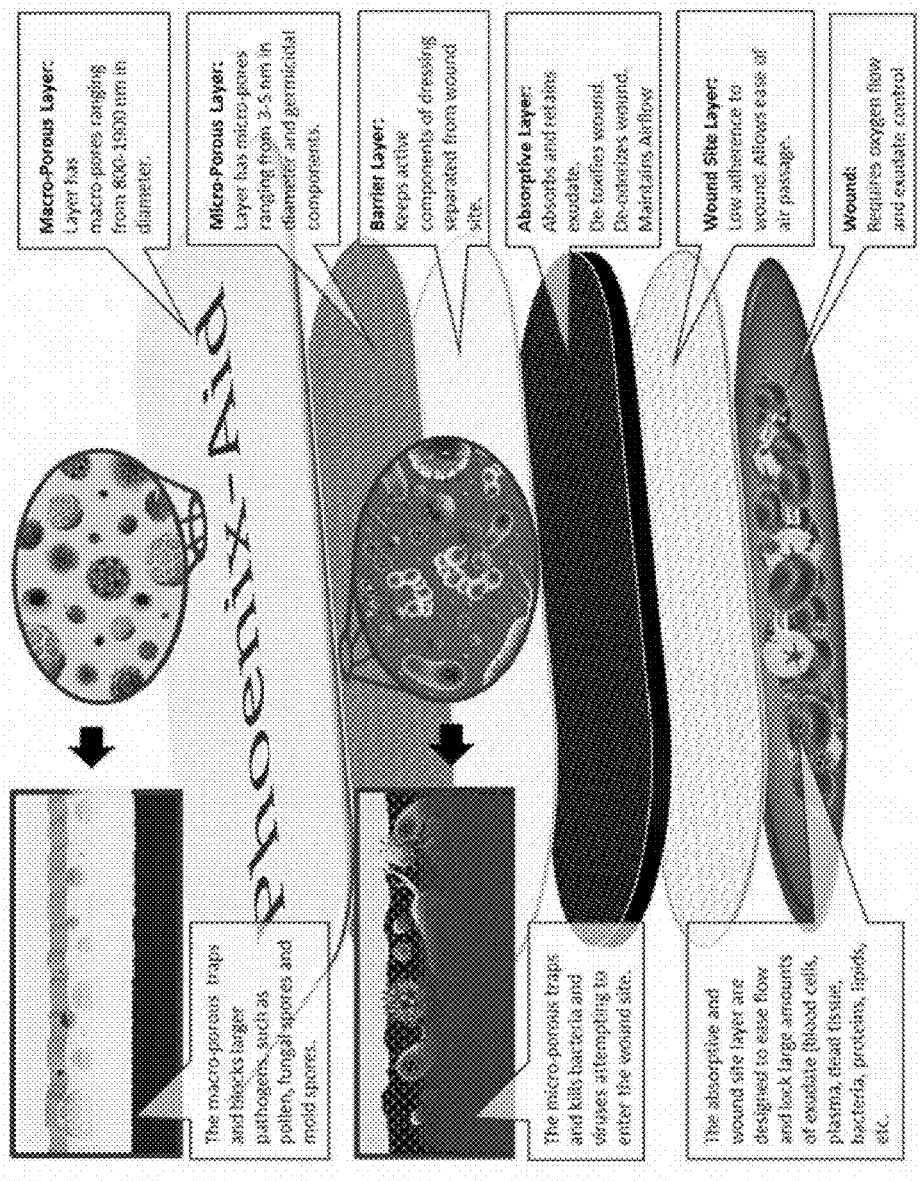
FIG. 4 is a diagram showing the layers of a preferred embodiment of the product with their respective purposes.
Figure 6:
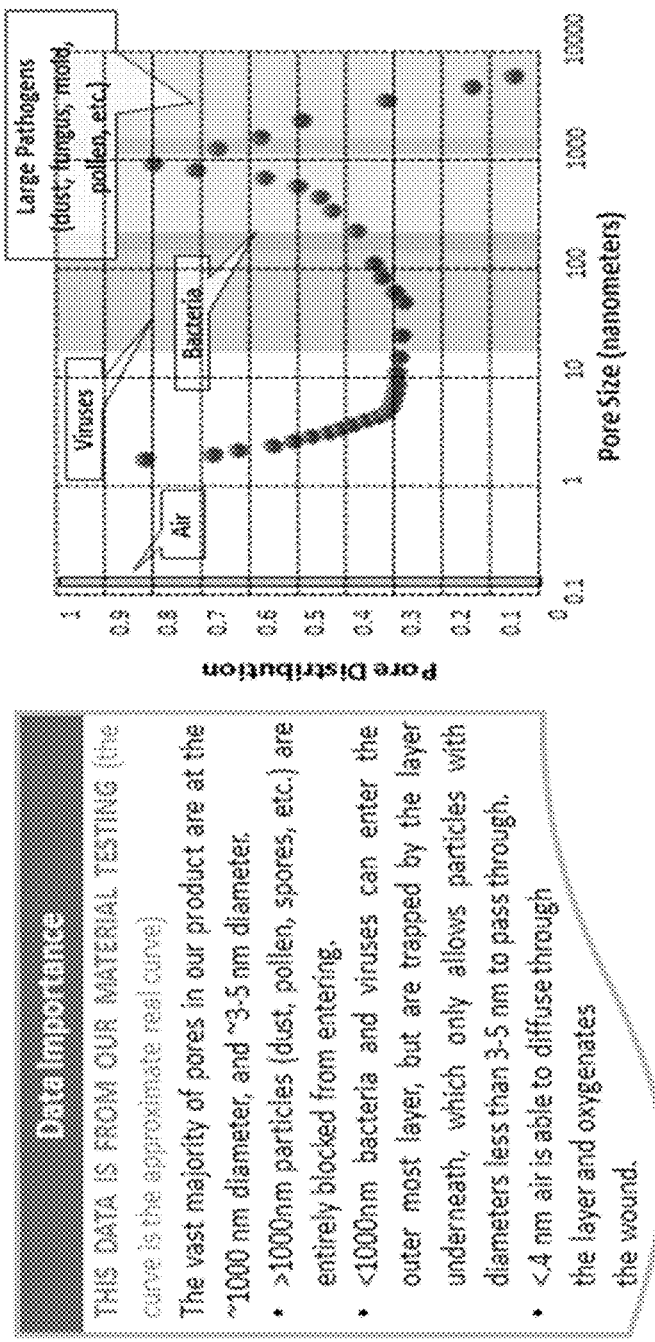
FIG. 6 is a diagram showing the results of invention porosity testing indicating that air is able to enter the wound, important for breathability, but contaminants like viruses, bacteria, and large pathogens cannot enter the wound.

Laboratory testing validates that together both the micro-porous and macro-porous layers comprise pores small enough to trap all or a clinically efficacious number of pathogens attempting to enter a wound site, but large enough to allow continuous or near-continuous airflow. The pores in the micro-porous layer are created, in one aspect, by creating a matrix with a polymer-activated carbon membrane. FIGS. 4 and 6 show that the layers are able to trap pathogens, while maintaining breathability.

One preferred embodiment has a fluid retention of 365 mg/cm, which is significantly above the vast majority of prior art products. Even with a relatively high amount of absorption, testing shows that the product exemplified herein is still breathable and only around 0.15 mm thick. One embodiment retains around 85% of the fluid absorbed after pressure is applied to the product, which exceeds most prior art products. Prior art with higher absorption and fluid retention does not include other key features of the current invention, including, but not limited to, high breathability, non-toxicity, water resistance, de-odorization of the wound, passive debridement, and inactivation of pathogens.

The absorptive composite layer as used in the manner taught herein reduce inflammatory responses, debride dead tissue, and detoxify and deodorize the wound. The absorptive layer, in one aspect, incorporates specialty powdered activated carbon, which has varying pore sizes to increase breathability, absorb organic and inorganic toxins, and decompose dead tissue to accelerate healing. FIG. 6 shows in detail how activated carbon can dissolve small and large organic molecules.

Each layer of the preferred five-layer embodiment is broken down and discussed in detail below.

Wound Site Layer (Also Referred to as Dual-Layer Healing Section):

This section consists of wound-site membrane and ternary composite absorption layer.

Overview

In embodiments, the wound site layer is mesoporous or macroporous. In aspects, it is a load-bearing layer, or a non-load bearing layer, made of a woven or unwoven, mesoporous, or macroporous membrane. The wound site layer is a single membrane or multiple membranes laminated together. In the preferred embodiment, this layer is designed, for example, to block skin debridement from entering the dressing, allow the free flow of atmospheric air, allow fluid passage to absorption layer, and allow for non-adherence of the wound dressing to the wound.

Composition Materials

In aspects, the wound site layer is made solely of, or a blend of, either a HEPA (highefficiency particulate air filter membrane), ULPA (ultra-low penetration air filter membrane), a combination of both HEPA and ULPA, unwoven or woven cotton, polyester, nylon, viscose or polypropylene textile fabric cloth, perforated silicone, and/or porous silicone. In aspects, the resulting membrane is hydrophilic and biocompatible.

Specific Preferred Combinations

A layer of a non-woven polypropylene, HEPA, ULPA, woven cotton, perforated silicone sheet, polyester, nylon, viscose or polypropylene textile fabric cloth based membrane, with a thickness of around 0.01 mm to 1.00 mm thickness, such as from 0.01 mm to 0.02 mm, from 0.02 mm to 0.03 mm, from 0.03 mm to 0.04 mm, and so on, is preferred. The wound side (bottom), may also be coated with a fine layer of activated carbon for enhanced wound debridement. A single treated side (top or bottom) may be treated for water resistance. A single coating side (top or bottom) of standard non-allergenic, or latex free adhesives, may be applied.

In another preferred embodiment, laminated layers of a non-woven polypropylene, HEPA, ULPA, woven cotton, polyester, nylon, perforated silicone sheet, viscose and/or polypropylene textile fabric cloth based membrane, totaling around 0.01 mm to 1.00 mm thick, such as from 0.01 mm to 0.02 mm, from 0.02 mm to 0.03 mm, from 0.03 mm to 0.04 mm, and so on, may be either heat pressed together, or adhered together with non-allergic or latex free adhesives. The wound side (bottom), may also be coated with a fine layer of activated carbon for enhanced wound debridement. The wound side (bottom), may also be coated with a fine layer of activated carbon for enhanced wound debridement. A single treated side (top or bottom) may be treated for water resistance. A single coating side (top or bottom) of standard non-allergenic, or latex free adhesives, may be applied.

Composite Absorption Layer:

Overview

In a preferred embodiment, the composite absorption layer is a microporous or mesoporous non-load-bearing layer, comprised of a polymer-carbon-absorbent composite. The pores are designed to allow the free flow of atmospheric air.

Composition Materials

In aspects, this polymer carbon composite is comprised of one or a combination of materials: (a) carbon, (b) germicidal ions, and (c) absorbent material. In one embodiment, the fabrication process comprises a (d) binding material, and (e) solvent. This layer is designed, for example, to absorb amounts of exudate, and to adhere to the insulating layer. Exudate includes, but is not limited to, cells and fluid, such as blood, plasma, puss, etc., that have seeped out of the wound site.

In aspects of material (a), the carbon may be activated carbon, powdered activated carbon, or activated carbon blended with graphene or activated carbon blended with nano-graphite powdered form, with grain/particle size in the range of around 25 µm to 75 µm in diameter; however, the grains/particles can range from 0.1 µm to 200 µm in diameter, such as from 0.1 µm to 0.2 µm, 0.2 µm to 0.3 µm, 0.3 µm to 0.4 µm, and so on. The activated carbon may be prepared by a specialized non-pyrolysis process with high levels of micropores and mesopores. The activated carbon may act as a host for germicidal ions and simultaneously play a role as a secondary absorbent. The activated carbon absorbs odors from the wound and toxic materials, and may assist to reduce the inflammation and aid a debridement process. The mass ratio of the carbon in the composite absorption layer may range from 0% to 65%, such as from 0% to 0.1%, 0.1% to 0.2%, 0.2% to 0.3%, and so on.

In aspects of material (b), the germicidal ions may comprise silver nitrate, nano-ionic silver, ionic silver, colloidal silver, ionic copper, colloidal copper, ionic arsenic, colloidal arsenic, ionic mercury, colloidal mercury, or combinations thereof. Alternatively, material (b) may also be forms of medical grade honey. In a preferred embodiment, the primary material used is silver nitrate, and it is impregnated into activated carbon at a primary concentration of around 1 mol/l; however, the concentration can range from 0.1 to 2 mol/l, such as from 0.1 to 0.2 mol/l, 0.2 to 0.3 mol/l, 0.3 to 0.4 mol/l, and so on. The impregnated carbon may later be reduced or not reduced to silver. An alternative material, colloidal silver, may be used, in one embodiment, at a primary concentration of around 10 parts per million; however, the concentration can range from 2 to 1000 parts per million, such as from 2 to 3 parts per million, from 3 to 4 parts per million, from 4 to 5 parts per million, and so on. An alternative material, colloidal copper, may also be used, in one aspect, at a primary concentration of around 10 parts per million; however, the concentration can range from 2 to 1000 parts per million, such as from 2 to 3 parts per million, from 3 to 4 parts per million, from 4 to 5 parts per million, and so on. An alternative material, colloidal mercury, may also be used, in one aspect, at a primary concentration of around 10 parts per million; however, the concentration can range from 2 to 1000 parts per million, such as from 2 to 3 parts per million, from 3 to 4 parts per million, from 4 to 5 parts per million, and so on. An alternative material, colloidal arsenic, may also be used, in one aspect at a primary concentration of around 10 parts per million; however, the concentration can range from 2 to 1000 parts per million, such as from 2 to 3 parts per million, from 3 to 4 parts per million, from 4 to 5 parts per million, and so on. By mass the concentrations of material (b) may range from 0% to 10%, such as from 0 to 1%, 1 to 2%, 2 to 3%, and so on.

Material (c), the primary absorbing material, may comprise either a superabsorbent polymer, such as sodium polyacrylate, polyacrylamide copolymer, etc., or cellulose, etc., or some combination thereof. In one embodiment, the primary material used is a specialty sodium polyacrylate blend specialized for blood or exudate absorption. In one aspect, the primary grains/particle size is around 44 µm to 88 µm in diameter; however, the grains/particles can range from 10 µm to 200 µm, or even around 0.300 mm in diameter. By mass the concentrations of material (c) range from 0% to 65%, such as from 0 to 1%, 1 to 2%, 2 to 3%, and so on.

Material (d), the binding material, can comprise silicone, polyvinylidene fluoride, polyvinyl chloride, or some combination thereof. The source material may be a liquid concentrate, liquid form, semi-solid gel, powder or paste form. By mass the concentrations of material (d) range from 0% to 65%, such as from 0 to 1%, 1 to 2%, 2 to 3%, and so on.

Material (e), the solvent, may comprise any liquid solvent which can dissolve material (d), the binding material. Material (e) may comprise either naphtha, n-methyl-2-pyrrolidone, denatured alcohol, or some combination thereof. Material (e) may be evaporated out during the layering and drying process. The mass of material (e) compared to the combined mass of materials (a, b, c and d) can range from 0% to 250%, such as from 0 to 1%, 1 to 2%, 2 to 3%, and so on.

In aspects, the resulting membrane is hydrophilic and biocompatible.

Specific Preferred Combinations

One example comprises a blend of (a) activated carbon, impregnated with (b) silver germicidal ions, of size around 100, 200, 325 mesh, (c) medical grade sodium polyacrylate and (d) medical silicone binder; mixed with (e) naphtha solvent.

One example comprises a blend of (a) activated carbon, impregnated with (b) silver germicidal ions, of size around 100, 200, 325 mesh, (c) medical grade sodium polyacrylate and (d) polyvinylidene fluoride; mixed with (e) n-methyl-2-pyrrolidone.

One example comprises a blend of activated carbon, (a) of size around 100, 200, or 325 mesh, (b) colloidal copper, (c) medical grade sodium polyacrylate (d), and pure medical silicone, mixed with (e) naphtha solvent, at mass concentrations as listed below, replacing activated carbon impregnated with silver germicidal ions with an activated carbon and colloidal copper mix. In this example, binder (d) can be polyvinylidene fluoride mixed with n-methyl-2-pyrrolidone as solvent (e).

One example comprises a blend of activated carbon, (a) of size around 100, 200, or 325 mesh, (b) colloidal silver, (c) medical grade sodium polyacrylate (d), and pure medical silicone, mixed with (e) naphtha solvent, at mass concentrations as listed below, replacing activated carbon impregnated with silver germicidal ions with activated carbon and colloidal silver. In this example, binder (d) can be polyvinylidene fluoride mixed with n-methyl-2-pyrrolidone as solvent (e).

In certain embodiments, the above combinations are made at the following mass concentrations:

Material (a+b): 40%; Material (c); 20%; Material (d): 40%;
Material (a+b): 45%; Material (c); 25%; Material (d): 30%;
Material (a+b): 50%; Material (c); 30%; Material (d): 20%;
Material (a+b): 40%; Material (c); 20%; Material (d): 40%;
Material (a+b): 33%; Material (c); 34%; Material (d): 33%;
Material (a+b): 33%; Material (c); 33%; Material (d): 34%;
Material (a+b): 35%; Material (c); 40%; Material (d): 25%;
Material (a+b): 40%; Material (c); 35%; Material (d): 25%;
Material (a+b): 50%; Material (c); 45%; Material (d): 5%;
Material (a+b): 50%; Material (c); 40%; Material (d): 10%;
Material (a+b): 52%; Material (c); 41%; Material (d): 7%.

Germicidal material (b) mass concentrations can range from: 0%, 1%, 2%, 3%, 4%, 5%, 6%, 7%, 8%, 9%, or 10%;

Solvent material (e) mass concentration can range from: 50%, 60%, 70%, 80%, 90%, 100%, 110%, 120%, 130%, 140%, 150%, 160%, 170%, 180%, 190%, or 200% of mass of combined mass of materials (a, b, c, and d).

The specific combinations listed above may also be coated on the insulating layer as described herein, using spray, casting, sputtering, evaporation, or other film application methods.

Tested Combinations

The following are a series of a few combinations already tested of the composition of the composite absorption layer:

See FIG. 18 (Absorption Layer)

Barrier or Insulating Layer (Ion-Barrier Layer):

Overview

In preferred embodiments, the insulating or barrier layer is a mesoporous or macroporous load-bearing layer (although it can be a non-load bearing layer) made of a woven or unwoven mesoporous or macroporous membrane. The barrier layer is designed to allow the free flow of atmospheric air and block or constrain the germicidal ions (b) from adjacent absorbent and seclusion layers.

Composition Materials

The insulating layer may comprise solely, or a blend of, a HEPA (high-efficiency particulate air filter membrane), ULPA (ultra-low penetration air filter membrane), or an unwoven or woven cotton, polyester, polypropylene, nylon, micro-cellulose, viscose, polypropylene textile fabric cloth, porous silicone, or perforated silicone membrane. In aspects, the resulting membrane is hydrophobic and biocompatible.

Specific Preferred Combinations

One example comprises a single layer of a HEPA, ULPA, unwoven cotton, woven cotton, polyester, polypropylene, nylon, microfiber, viscose or polypropylene textile fabric cloth, perforated silicone, or perforated silence membrane around 50 µm to 200 µm thick.

With a single treated side (top or bottom) for water resistance.
With a single coating side (top or bottom) of standard non-allergenic, or latex free adhesives.
Without a single coating side (top or bottom) of standard non-allergenic, or latex free adhesives.
Without a single treated side for water resistance
With a single coating side (top or bottom) of standard non-allergenic, or latex free adhesives.
Without a single coating side (top or bottom) of standard non-allergenic, or latex free adhesives.

Another example comprises composite layers of a HEPA, ULPA, polyester, polypropylene, nylon, microfiber, viscose, polypropylene textile fabric, perforated silicone or porous silicone, which may be around 50 µm to 200 µm thick, and heat pressed together or adhered together with non-allergic or latex free adhesives.

With a single treated side (top or bottom) for water resistance.
With a single coating side (top or bottom) of standard non-allergenic, or latex free adhesives.
Without a single coating side (top or bottom) of standard non-allergenic, or latex free adhesives.
Without a single treated side for water resistance
With a single coating side (top or bottom) of standard non-allergenic, or latex free adhesives.
Without a single coating side (top or bottom) of standard non-allergenic, or latex free adhesives.

Seclusion Layer (Micro-Porous/Germicidal Layer):

In one embodiment, the seclusion layer may comprise a microporous non-load-bearing layer, comprised of a polymer-activated carbon composite. Microporous, in one particular aspect, includes a pore size of less than around 2-5 nm in diameter. These pores are designed to host germicidal ions and deactivate and kill relatively small external pathogens, and allow the free flow of atmospheric air. The micropores are used to host the germicidal ions that kill pathogens. Such small external pathogens include microbes, such as bacteria, prions and viruses, which are found in the external environment, and may or may not have ill effects if in contact with human skin.

These external pathogens may reside in the atmosphere, vapor, contact surfaces, or liquid bodies. This layer, in one aspect, is designed to block small external pathogens, kill or otherwise inactivate small external pathogens, allow the free flow of atmospheric air, and/or adhere to the top layer. This layer secludes the wound site and absorbent layer from external contaminants.

Composition Materials

In one example, the seclusion layer comprises a polymer carbon composite, which is comprised of a combination of materials: (a1) activated carbon impregnated with (b1) germicidal ions, (d1) binding material, and (e1) solvent. These materials are as defined as in the absorbent layer; however, they have different characteristics and compositions.

Specific Preferred Combinations

In one embodiment, the layer comprises a blend of powdered activated carbon, (a1) of size of around 100, 200, or 325 mesh, impregnated with silver germicidal ions (b1) and medical silicone binder (d1), mixed with naphtha solvent (e1), at following mass concentrations:

Material (a1+b1): 60% and Material (d1): 40%
Material (a1+b1): 55% and Material (d1): 45%
Material (a1+b1): 50% and Material (d1): 50%
Material (a1+b1): 45% and Material (d1): 55%
Material (a1+b1): 40% and Material (d1): 60%
Material (a1+b1): 35% and Material (d1): 65%
Material (a1+b1): 30% and Material (d1): 70%
Material (a1+b1): 90% and Material (d1): 10%
Material (a1+b1): 85% and Material (d1): 15%
Material (a1+b1): 80% and Material (d1): 20%

Germicidal material (b1) may range from: 0%, 1%, 2%, 3%, 4%, 5%, 6%, 7%, 8%, 9%, or 10%;

Solvent material (e1) may range from: 50%, 60%, 70%, 80%, 90%, 100%, 110%, 120%, 130%, 140%, 150%, 160%, 170%, 180%, 190%, or 200% by mass of combined mass of materials (a1, b1, and d1).

In another embodiment, binder (d) can be polyvinylidene fluoride mixed with n-methyl-2-pyrrolidone as solvent (e), at various mass concentrations.

In another example, the layer comprises a blend of activated carbon, (a1) of size of around 100, 200, or 325 mesh, mixed with colloidal copper germicidal ions (b1), and pure medical silicone (d1), of concentrations and solvent (e1) proportions as listed above. In this example, binder (d) can be polyvinylidene fluoride mixed with n-methyl-2-pyrrolidone as solvent (e).

In another example, the layer comprises a blend of activated carbon, (a1) of size of around 100, 200, or 325 mesh, mixed with colloidal silver germicidal ions (b1), and pure medical silicone (d1), of concentrations and solvent (e1) proportions as listed above. In this example, binder (d) can be polyvinylidene fluoride mixed with n-methyl-2-pyrrolidone as solvent (e).

Alternatively, material (b1) may also be forms of medical grade honey.

Tested Combinations

The following are a series of a few combinations already tested of the composition of the composite absorption layer:

See FIG. 19 (Seclusion Layer)

Top or Outer Layer:

In a preferred embodiment, the top layer comprises a mesoporous or macroporous load bearing layer comprising a woven or unwoven mesoporous or macroporous membrane. In aspects, the mesoporous layer includes a pore size of around 6-50 nm in diameter. In aspects, the macroporous layer includes a pore size of around 50-500 nm in diameter. These pores are designed to trap relatively large pathogens, and allow the free flow of atmospheric air. Large external pathogens include, but are not limited to, dust, dirt, debris, mites, pollen, fungal spores, or mold spores, which are found in the external environment, and may or may not have ill effects if in contact with the human skin. These large external pathogens may reside in the atmosphere, contact surfaces, or liquid bodies. The inner surface of the layer, towards a wound site, in aspects, has adhesion coatings. In a preferred embodiment, the top layer is designed to block large external pathogens, allow the free flow of atmospheric air, be water resistant, load bearing, and receptive to adhesion coatings on one side of the layer.

Composition Materials

The top layer comprises solely, or a blend of, HEPA (high-efficiency particulate air filter membrane), ULPA (ultra-low penetration air filter membrane), micro-cellulose, polyester, polypropylene, nylon, microfiber, viscose, cotton fabric tape, polypropylene textile fabric cloth, perforated silicone, or porous silicone.

Specific Preferred Combinations

In one example, the top layer comprises a single layer of a HEPA, ULPA, polyester, polypropylene, nylon, microcellulose, viscose, cotton fabric tape, polypropylene textile fabric cloth, perforated silicone or porous silicone based membrane, around 50 µm to 500 µm thick.

With a single treated side (top or bottom) for water resistance.
With a single coating side (top or bottom) of standard non-allergenic, or latex free adhesives.
Without a single coating side (top or bottom) of standard non-allergenic, or latex free adhesives.
Without a single treated side for water resistance.
With a single coating side (top or bottom) of standard non-allergenic, or latex free adhesives.
Without a single coating side (top or bottom) of standard non-allergenic, or latex free adhesives.

In another example, the layer may comprise laminate of a HEPA, ULPA, polyester, polypropylene, nylon, microcellulose, viscose, cotton fabric tape, polypropylene textile fabric cloth or porous silicone based membrane, around 50 µm to 500 µm thick, which are heat pressed together or adhered together with non-allergic or latex free adhesives.

With a single treated side (top or bottom) for water resistance.
With a single coating side (top or bottom) of standard non-allergenic, or latex free adhesives.
Without a single coating side (top or bottom) of standard non-allergenic, or latex free adhesives.
Without a single treated side for water resistance.
With a single coating side (top or bottom) of standard non-allergenic, or latex free adhesives.
Without a single coating side (top or bottom) of standard non-allergenic, or latex free adhesives.

Layering Process:

Overview

In the preferred embodiment, the invention comprises a biocompatible cloth comprising five layers. Going from the wound site to outer atmospheric side, the layers are Wound-site layer (1): load bearing, or non-load bearing; Composite absorption Layer (2): non-load bearing; Ion barrier Layer (3): load bearing or non-load bearing; Seclusion Layer (4): non-load bearing, and Outer Layer (5): load bearing.

Example: Process method 1: Micro-film application

[0105] Layer (1):

In one aspect, the material for layer (1) is spooled into a roll and cut to the required width to encapsulate non-load bearing layer (2). This layer is optionally treated for higher water/fluid absorption from the wound site. While layer (2) or multi-layer coating comprising layers (2) and (4) are cured on insulting layer (3), layer (1) is fed and compressed, rolled, cured, dried and sterilized, as needed.

Layer (2):

In one aspect, materials (a and c) are grinded down to a desired mesh size. Here, material (b) is impregnated into material (a) or added as a component additive at later stages of mixing. They are then mixed together in a dry ball mill machine. Material (d), which is kept in a gel form, is then added together with Material (a and c) into a mixer and blended. Material (e) is poured into the mixer with materials (a, c, and d). Once the mixture of materials (a, c, d, and e) is homogenous, material (b) is added to the mixture and stirred. The viscosity of the mixture is tailored by material (e) until a slurry suitable for tape-casting, or dip-coating or film coating on a substrate is achieved. Moderate amount of dispersant and plasticizer is added to certain compositions of the mixer in order to achieve the required rheological properties of the slurry.

The mixture is continuously stirred to maintain homogenous form and casted on a substrate using a microfilm applicator and set to the desired thickness. Here the substrate is a surface of any of the adjacent layers (layer 1 or 3 or layer 3 pre-coated with layer 4) depending upon composition of the slurry and its targeted functionality.

Layer (3):

In one aspect, the material for layer (3) is spooled into a roll, and cut to the required width that is larger than the width of the adjacent layers (2 and 4). This layer is optionally treated to increase hydrophobic properties. This layer serves as a substrate for coating layers (2 and 4) by film casting or spraying as desired. The coated insulating layer is optionally compressed by rollers over the conveyer belt system, so as to eliminate air bubbles, and to ensure uniform thickness and bonding. The procedure is repeated when the coating is carried out on the other surface. Appropriate treatments are carried out down the conveyer line to cure or dry or sterilize the coated layer as needed.

Layer (4):

In one aspect, material (a1) is grinded down to a desired mesh size. Material (b1) is impregnated into material (a1) or added as a component additive at later stages of mixing. Material (d1), which is kept in a gel form, is then added to (a1) and blended. Material (e1) is poured into the mixer with materials (a1 and d1). Once the mixture of materials (a1, d1, and e1) is homogenous, material (b1) is added to the mixture, and stirred, until materials (a1, b1, d1, and e1) are homogenous. The viscosity of the mixture is tailored by material (e1) until a slurry suitable for tape-casting, or dip-coating or film coating on a substrate is achieved. Moderate amount of dispersant and plasticizer is added to certain compositions of the mixer in order to achieve the required rheological properties of the slurry. This layer is optionally treated for higher water/fluid repulsion from an outer layer.

Layer (5):

In one aspect, the material for layer (5) is spooled into a roll. One side of the roll (top) is optionally treated to increase water resistance or make it waterproof. The other side of the roll (bottom) is optionally coated with adhesives. The roll is then fed into a line conveyor belt, where the (bottom) of layer (1) is laying upwards.

Adhesion Edges or Rings:

In one aspect, the outer edges of the insulating layer (3) are coated with a bio-compatible adhesive ring. This adhesive bondage isolates and protects the wound site from lateral exudate seepage. The outer-layer (5) is also provided with an adhesion ring, which encapsulates all the other layers to protect the wound site from external influences.

Example: Process Method 2: Spray-Film Application

Layer (1):

In one aspect, the material for layer (1) is spooled into a roll, and cut to a desired width to encapsulate non-load bearing layer (2). This layer is optionally treated for higher water/fluid absorption from the wound site. While layer (2) or multi-layer coating comprising layers (2) and (4) is curing on insulting layer (3), layer (1) is fed and compressed, rolled, cured, dried and sterilized as needed.

Layer (2):

In one aspect, materials (a and c) are grinded down to a desired mesh size. Material (b) is impregnated into material (a) or added as a component additive at later stages of mixing. They are then mixed together in a dry ball mill machine. Material (d), which is kept in a gel form, is then added together with material (a and c) into a mixer and blended. Material (e) is poured into the mixer with materials (a, c, and d). Once the mixture of materials (a, c, d, and e) is homogenous, material (b) is added to the mixture and stirred. The viscosity and specific gravity of the mixture is tailored by material (e) to obtain a liquid solution suitable for spray coating. The solution is filtered and loaded to a spray reservoir. Ultrasound treatment (sonification) is carried out to maintain homogeneity of the solution. The substrate material (3 or 1) is fed through a conveyer belt, underneath an ultrasonic or spray applicator set to a determined nozzle dispersion rate. The substrate and spray coated membrane is compressed, rolled, cured, dried and sterilized as needed.

Layer (3):

In one aspect, the material for layer (3) is spooled into a roll, and cut to a desired width that is larger than the width of the adjacent layers (2 and 4). This layer is optionally treated to increase hydrophobic properties. This layer serves as a substrate for coating layers (2 and 4) by film casting or spraying as desired. The coated insulating layer compressed by rollers over the conveyer belt system, so as to eliminate air bubbles, and to ensure uniform thickness and bonding. The procedure is repeated when the coating is carried out on the other surface. Appropriate treatments are carried out down the conveyer line to cure or dry or sterilize the coated layer as needed.

Layer (4):

In one aspect, material (a1) is grinded down to a desired mesh size. Material (b1) is impregnated into material (a1) or added as a component additive at later stages of mixing. Material (d1), which is kept in a gel form, is then added to (a1) and blended. Material (e1) is poured into the mixer with materials (a1 and d1). Once the mixture of materials (a1, d1, and e1) is homogenous, material (b1) is added to the mixture, and stirred, until materials (a1, b1, c1, d1, and e1) are homogenous. The viscosity and the specific gravity of the solution is tailored by material (e1) until it is suitable for spray coating on a substrate. This layer is optionally treated for higher water/fluid repulsion from an outer layer. The solution is filtered and loaded to a spray reservoir. Ultrasound treatment (sonification) is carried out to maintain homogeneity of the solution. The substrate material (3) is fed through a conveyer belt, underneath an ultrasonic or spray applicator set to a determined nozzle dispersion rate. The substrate and spray coated membrane are compressed, rolled, cured, dried and sterilized as needed.

The conveyer belt is then fed into an air low convection air dryer, at temperatures of around 25 degrees Celsius to 65 degrees Celsius. Once layer (2) is dry, it forms a bond with both layer (1) and layer (3).

Layer (5):

In one aspect, the material for layer (5) is spooled into a roll. One side of the roll (top) is optionally treated to increase water resistance or make it waterproof. The other side of the roll (bottom) is optionally coated with adhesives. The roll is then fed into a line conveyor belt, where the (bottom) of layer (1) is laying upwards.

Adhesion Edges or Rings:

In one aspect, the outer edges of the insulating layer (3) are coated with a bio-compatible adhesive ring. This adhesive bondage isolates and protects the wound site from lateral exudate seepage. The outer-layer (5) is also provided with an adhesion ring, which encapsulates all the other layers to protect the wound site from external influences.

Specific Process Method Example: (See FIG. 17)

Layer 1: Air side layer, perforated, hydrophobic (or water resistant); for example, perforated cloth or other woven/non-woven material or surgical tape with adhesives on one side.

Layer 3: Macro-porous roll membrane. Ex. Polypropylene.

Layer 2: Polymer-Carbon composite slurry-2 (provided with thinner-2). Coated directly on Layer 3 and cured.

Layer 4: Polymer-Carbon composite slurry-4 (provided with thinner-4). Coated directly on Layer 3, on the uncoated side) and cured. If needed, multiple coats can be applied to reach a desired thickness; however, a single coat is preferred.

If needed, Layer-4 can be coated first and then Layer-2 can be coated. Both layers 2 and 4 will dry to less than 60% of coated (wet) thickness in embodiments.

Layer 5: Wound contact layer. Perforated roll membrane. Allows free-flow of exudate to layer 4. Ex. Perforated silicone Details and Materials Layer 1: Wound-Site Side Layer Functionalities: Bio-compatible. Hypoallergenic. Perforated to allow quick exudate passage directly to layer 4. Preferably wicks exudate evenly across layer 4.

Properties: Porous with adhesives on one side.

Materials: Perforated with adhesive on one-side supplied (Ex. Silicone membrane).

Preferred sizes: Width 13 cm, thickness of 0.2 mm, pore size of ~100-500 um (Pore density>15%).

Layer 2: To be Coated on Layer-3

Layer 2 in embodiments comes in a viscous liquid form and is comprised of Polymer-Carbon composite polymer slurry-2 which needs to be kept in a sealed container (moisture sensitive), before assembly. The viscosity for coating conditions can be optimized using the thinner (thinner-2). The organic solvents/thinner evaporate leaving an active material coating on Layer-3. Curing conditions can be thermal (electric or IR). Certain optimization is required to avoid cambering.

Preferred sizes: Width 8.0 cm and Cured Thickness 0.4 mm (wet thickness is ~2×).

Layer 3: Support Layer:

Functionalities: Allows free flow of air. Hypoallergenic.

Properties: Macroporous. Flexible and mechanically robust. Ability to withstand coating conditions of layer-2 and layer-4 for wettability and curing treatments (thermal, IR and UV). Hydrophobic.

Materials: Non-woven polymeric membrane with pores (Ex. Polypropylene membrane rolls).

Preferred sizes: Width of 12 cm, thickness of 0.2 mm, pore size of 5 to 30 um.

Layer 4: To be Coated on Layer-3

Layer 4 may come in a viscous liquid form and is comprised of Polymer-Carbon composite polymer slurry-4 which needs to be kept in a sealed container (mildly moisture sensitive), before assembly. The viscosity for coating conditions can be optimized using the thinner (thinner-4). The organic solvents/thinner evaporate leaving an active material coating on Layer-3. Curing conditions can be thermal (electric or IR). Certain optimization is required to avoid cambering.

Preferred sizes: Width of 10.0 cm and Cured Thickness 0.1 mm (dry) (wet thickness is ~2×).

Layer 5: Air-side Layer or the Outer Porous Layer.

Functionalities: Block dust and dirt, mites, pollen, fungal spores, or mold spores. Allows free flow of air. Hypoallergenic.

Properties: Flexible. Hydrophobic or water resistant. Sterilizable.

Materials: Perforated with adhesive on one-side supplied (Ex. Porous surgical tape). Preferred sizes: Width of 15 cm, thickness of 0.2 mm, pore size range 50 to 250 um.

Embodiment of Process Steps:

1. Liquid coating of layer-4 on layer-3 and curing (and twin-rolling as needed);
2. Liquid coating of layer-2 on uncoated side of layer-3 and curing (single-step or multi-step coating as needed), subsequent curing (and twin-rolling as needed);
3. Adhesion of layer-5 on coated assembly (Layer 2, 3, and 4);
4. Adhesion and sealing of Layer-1 on to the above;
5. Final curing, pressing or treatment (IR or UV) as needed; and
6. Packaging (as rolls or individual squares). Sterilization ready.

Data

Figure 10:
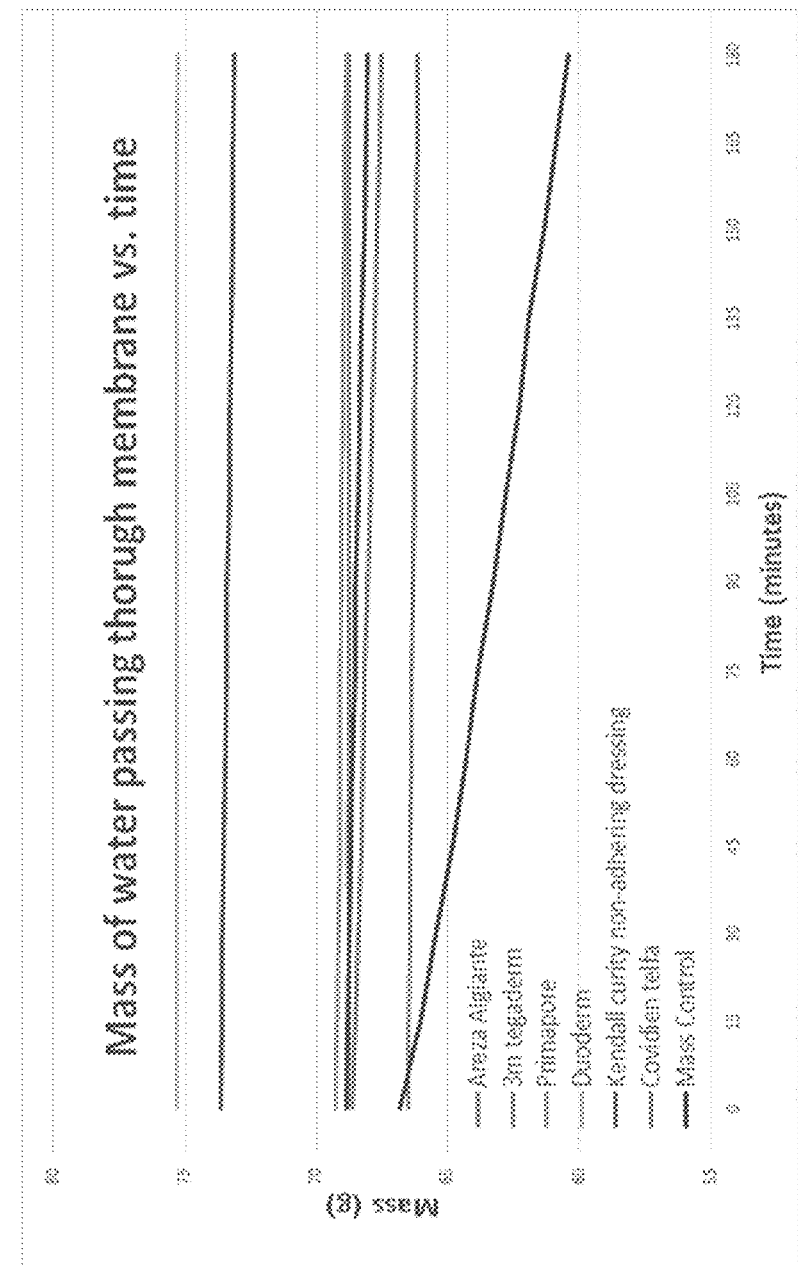
FIG. 10 is a diagram showing retention results indicating breathability over time.
Figure 12:
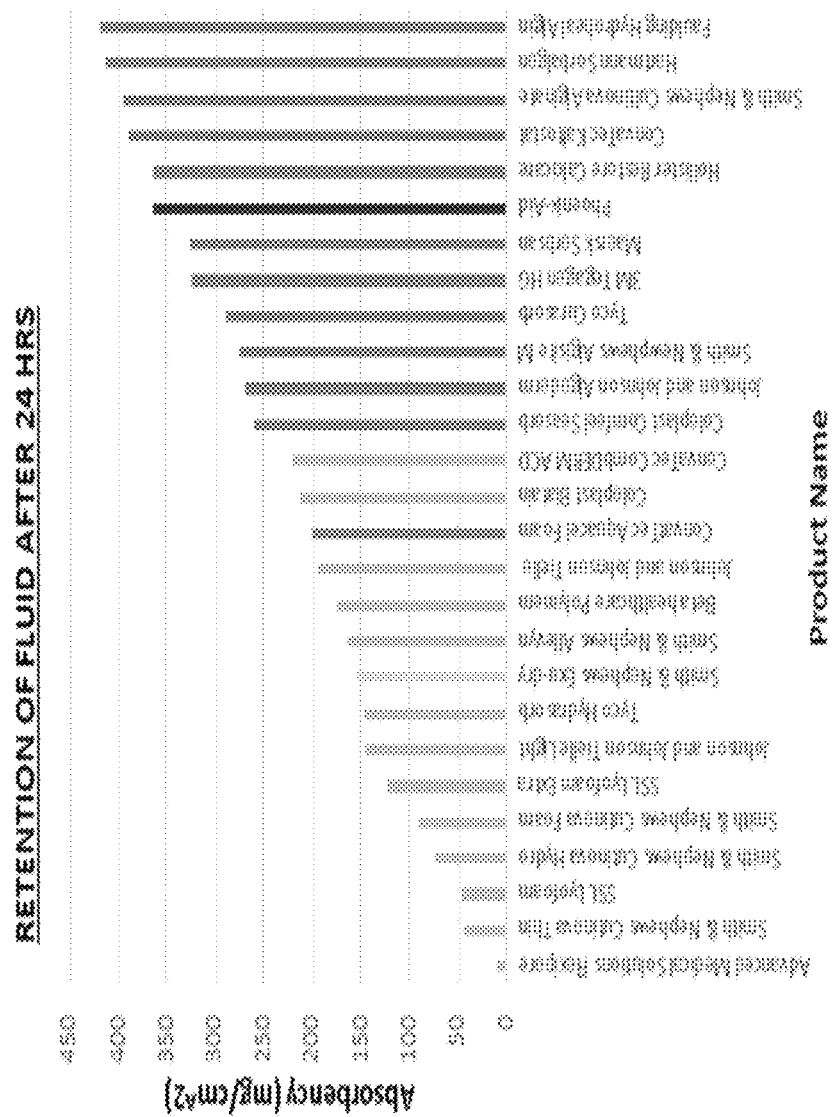
FIG. 12 is a diagram showing absorbency results place the invention near the top of dressings tested.
Figure 13:
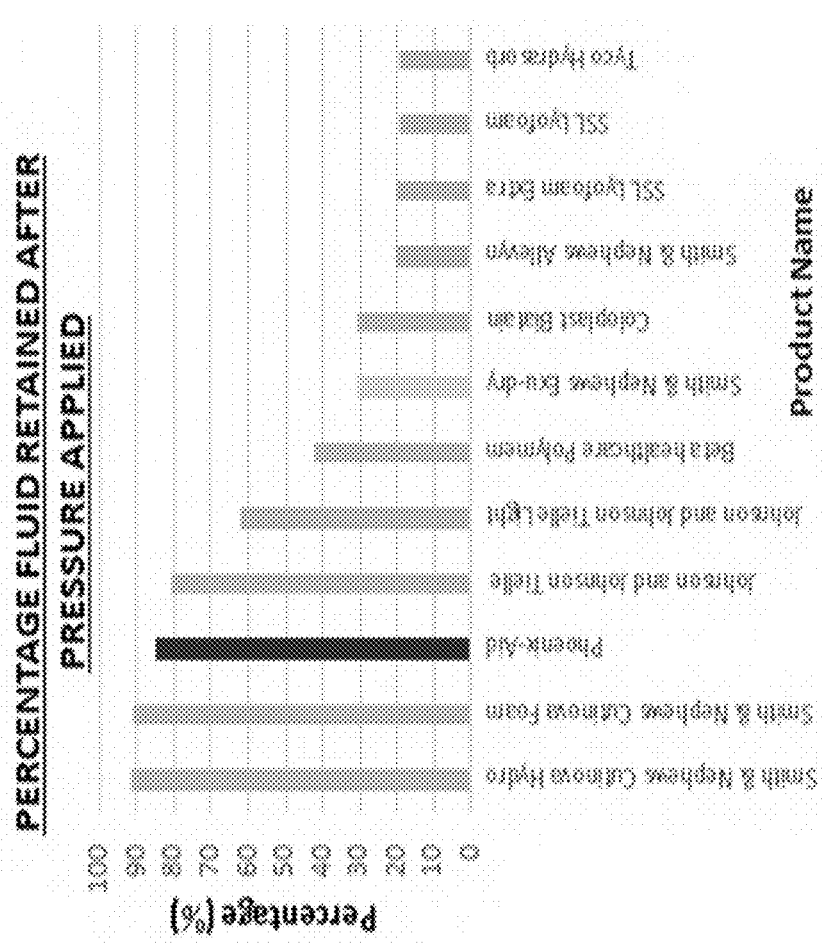
FIG. 13 is a diagram showing liquid retained after applied force testing places the invention close to the top of products tested.
Figure 14:
FIG. 14 is a diagram showing durability testing results.
Figure 15:
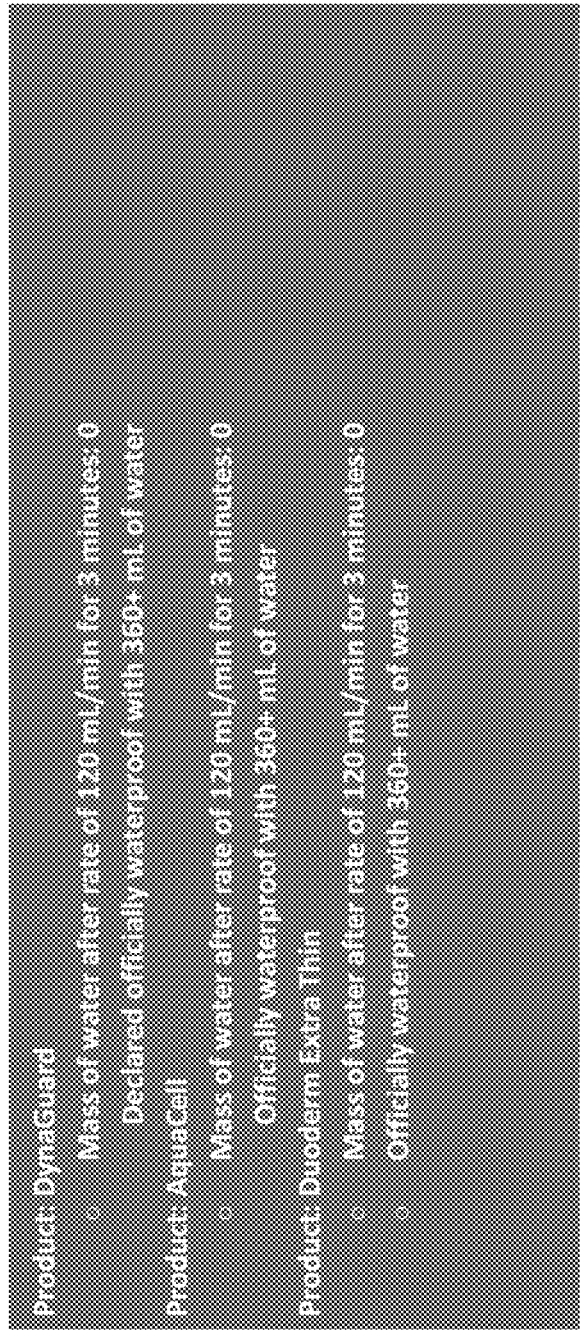
FIG. 15 is a diagram showing waterproof testing results.
Figure 16:
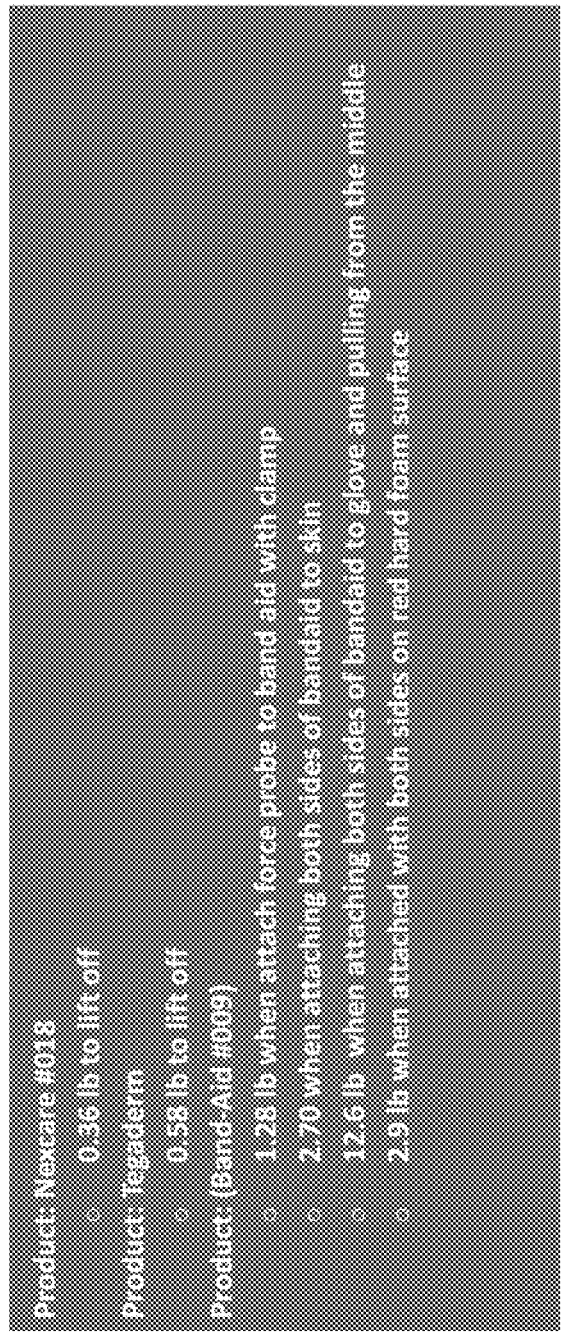
FIG. 16 is a diagram showing adhesion testing results.

Breathability of the invention was tested by running membranes through a wind tunnel, with one end capped over a beaker containing water. The more breathable the product, the more water would evaporate. FIG. 10 showcases the graph trends, while FIG. 11 (Table 1) showcases the data. In a preferred embodiment, the invention also absorbs exudate, such as blood and plasma. FIG. 12 shows comparative data on absorption amounts over 24 hours. Coupled with absorption is fluid retention, an important characteristic to demonstrate the ability of the membrane to hold fluid if a force, such as rolling over in bed, is applied. FIG. 13 shows comparative data on fluid retention after a 20-kg mass is applied. FIG. 14 (Table 2) shows comparative tests on products running through an Instron machine. FIG. 15 (Table 3) shows comparative tests on waterproofness by measuring the height of a water column over products. FIG. 16 (Table 4) shows comparative tests on adhesion, by using a force probe to lift a product from an imitation skin surface.

Alternatives

The technology described herein can used in a variety of wounds by varying the material compositions as explained herein. The invention can be applied to a variety of wound care specialties, including, but not limited to, bed sores, pressure ulcers, surgical wounds, trauma wounds, gunshot wounds, stab wounds, small lacerations, large lacerations, chronic wounds, small acute wounds, large acute wounds, etc.

Alternate Versions

The technology can also be separated into two separate sections. The first section, in one particular embodiment, comprises the wound site layer, the absorption layer, and optionally the ion barrier layer. Section two comprises the seclusion layer, the outer layer, and optionally the ion barrier layer. Both section 1 and 2 may have the ion barrier layer simultaneously.

Section 1 may be created using either method one, or two (with only the layers used in section 1). If section 1 does not have the ion barrier layer, to use as a load bearing layer, the wound site layer acts as a load bearing layer. Section 1 is optionally not covered with any adhesives. Section 1 is optionally covered with adhesives on the wound site layer.

Section 2 may be created using either method one, or two (with only the layers used in section 2). If section 2 does not have the ion barrier layer, to use as a load bearing layer, the outer layer acts as a load bearing layer. Section 2 is optionally not covered with any adhesives. Section 2 is optionally covered with adhesives on the ion barrier layer. If the ion barrier is not used in section 2, section 2 is optionally covered with adhesives on the seclusion layer.

Section 1, in one aspect, is put directly on the wound, and may be cut, from a roll, to any desired length. If needed, section 1 may also be folded, cut in half, or stacked, to form a thicker covering to the wound. In one aspect, section 2 is put over section 1, with an overlap to form a seal over the wound. If needed section 1 may also be folded, cut in half, or stacked, to form a thicker covering over section 2.

In another possible embodiment, the dressing can be made into a 3-layer dressing, comprising the macro-porous layer, the absorption layer, and the wound site layer, and removing the micro-porous layer and the ion-barrier layer. In aspects, this combination is suited for lower exuding wounds, which have a lower chance of infection. The macro-porous layer, in a preferred embodiment, is adjacent to the absorbent layer, comprising a polymer-carbon composite which may or may not contain germicidal ions. The absorbent layer, in aspects, is adjacent to a wound-site layer. The macro-porous layer may or may not have adhesive(s); the wound site layer may or may not have adhesive(s).

The technology can also be applied in other forms of products including, but not limited to, diapers, tampons, pads, etc. In a test using the described invention for a tampon, the tampon was able to control oxygen flow through a tapered design, and had a low friction adherence as well as rigidity for ease of input and prevention of tearing. Using the carbon-polymer blend, the tampon can actively prevent bacterial infections, and in laboratory tests, it was shown that the tampon product absorbed toxins along with high volumes of exudate. Menstruating women who use tampons are at risk of several complications, including toxic shock syndrome, which can lead to mineral and fluid leakage from the vital organs, decreased blood supply, and even serious cases such as coma and death. The tampon product using the invention taught herein is ideal for preventing toxic shock syndrome and complications from tampons. A menstrual tampon is a device that is a plug made of cellulosic or synthetic material that is inserted into the vagina and used to absorb menstrual or other vaginal discharge. It allows women to be far more active and less self-conscious than utilizing a traditional pad for protection. More than a third of all cases of toxic shock involve women under 19, and up to 30% of women who have had the disease will get it again. A tampon saturated with blood is a supportive place for rapid growth of bacteria. The method in which bacterial poisons enter the bloodstream is heavily related to tampon use. Sliding a tampon into place in the vagina may make microscopic tears in the walls of the vagina, rupturing tiny blood vessels. A superabsorbent tampon, especially one that lasts longer than the usual 4-5 hour capacity of many tampons, is needed to provide maximum support for women during their menstrual period.

Figure 2:
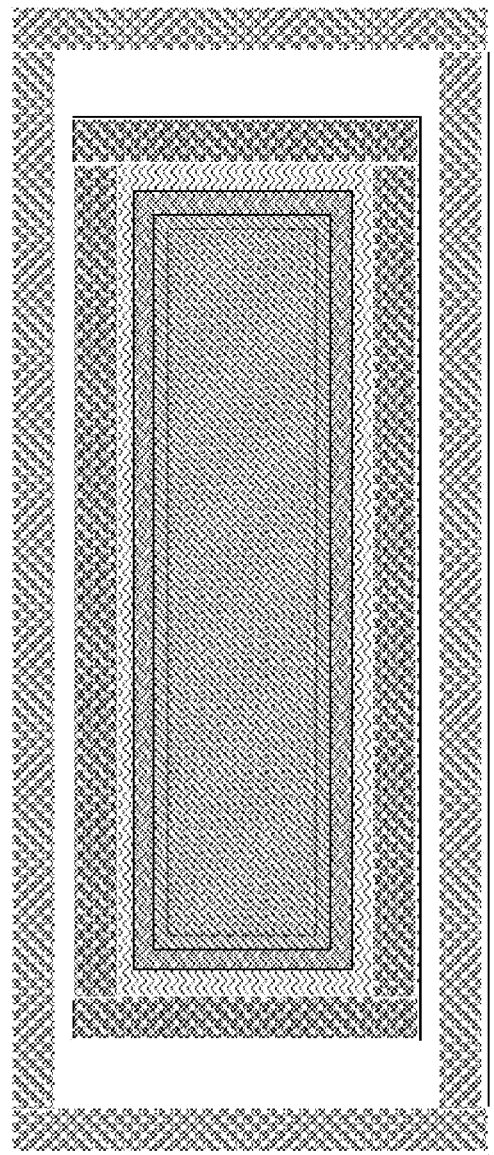
FIG. 2 is a schematic showing the bottom or wound site view of the dressing illustrating two zone adhesion edges.

Turning to the figures, FIG. 1 shows a possible embodiment of the current invention showing five layers as described above. FIG. 2 shows a top view of the dressing with five layers as oriented on the dressing.

Figure 3:
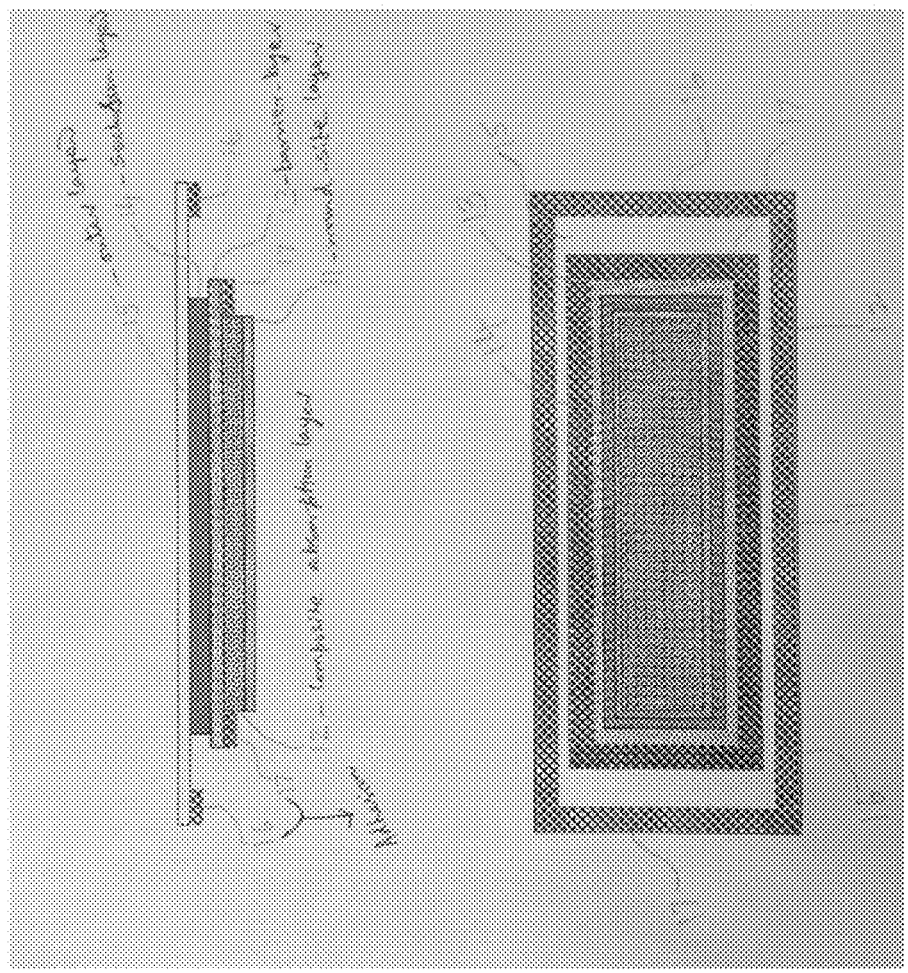
FIG. 3 is a schematic showing the side view of FIG. 1 and bottom view of FIG. 2, with annotations.

FIG. 3 shows a top and side view of a possible five layer embodiment of the invention. In FIG. 3, the outer layer 15 is shown above the seclusion layer 14. The seclusion layer is above the barrier layer 13 and the barrier layer is over a composite absorption layer 12. At the bottom is the wound site layer 11. Included are different possible sites for adhesives or full or partial adhesion layers 16, 17.

FIG. 4 shows in a diagram functions and explanations of various layers.

Figure 5:
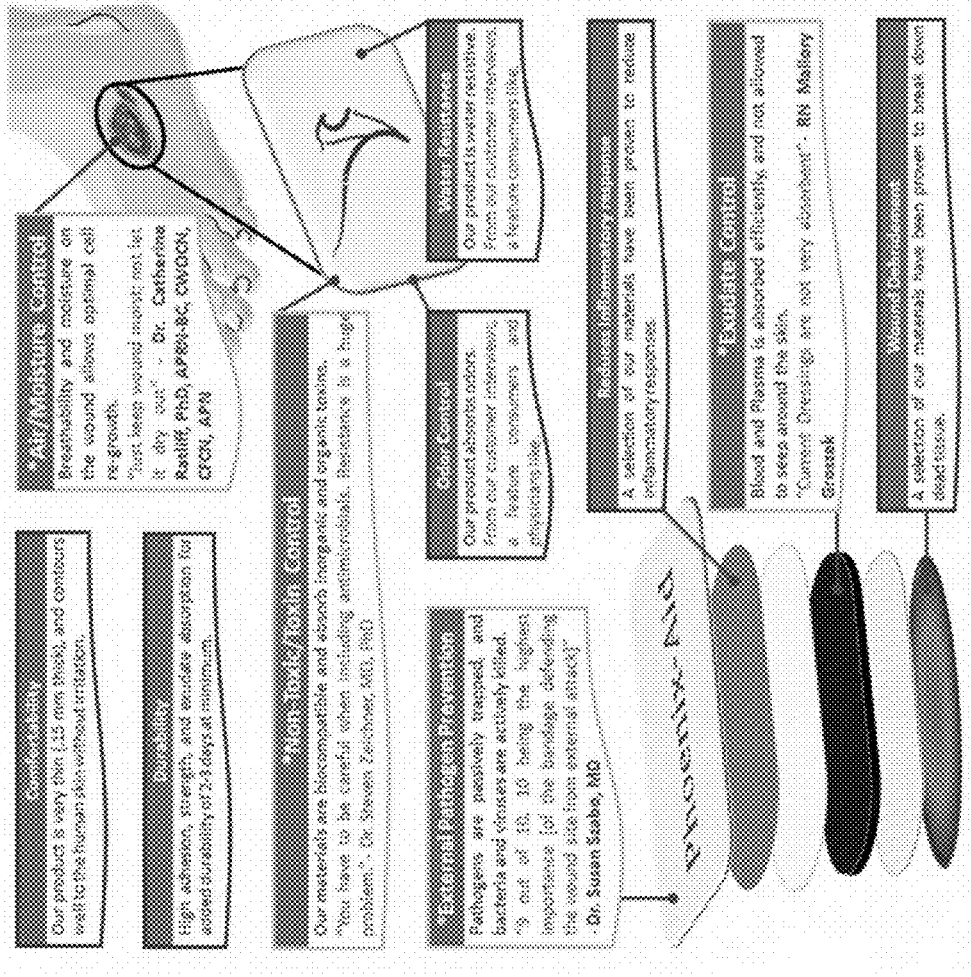
FIG. 5 is a diagram showing efficacious elements of a preferred embodiment of the present invention.

FIG. 5 shows in a diagram functions and explanations of various layers.

FIG. 6 is a diagram showing the results of invention porosity testing indicating that air is able to enter the wound, important for breathability, but contaminants like viruses, bacteria, and large pathogens cannot enter the wound.

Figure 7:
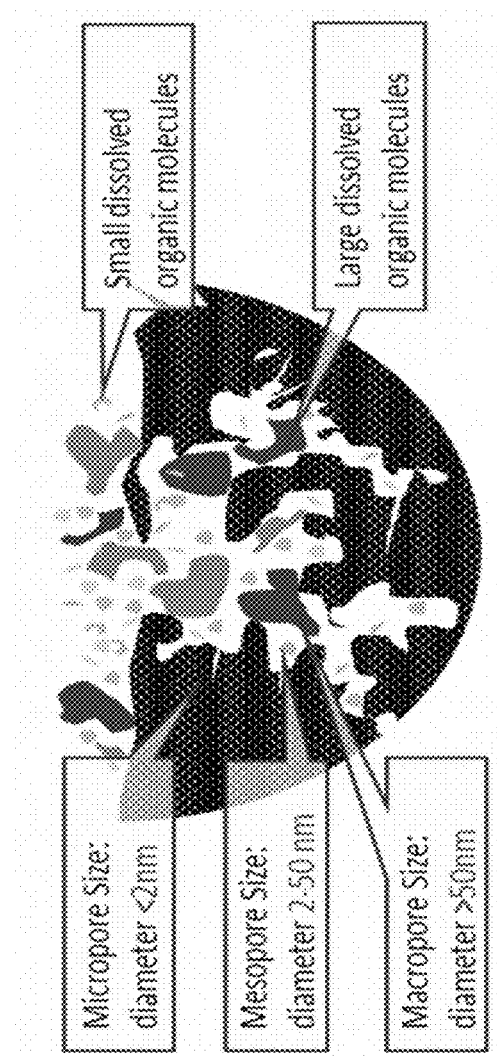
FIG. 7 is a diagram showing the breakdown of the activated carbon used in a preferred embodiment of the invention.

FIG. 7 is a diagram showing the breakdown of the activated carbon used in a preferred embodiment of the invention.

Figure 8:
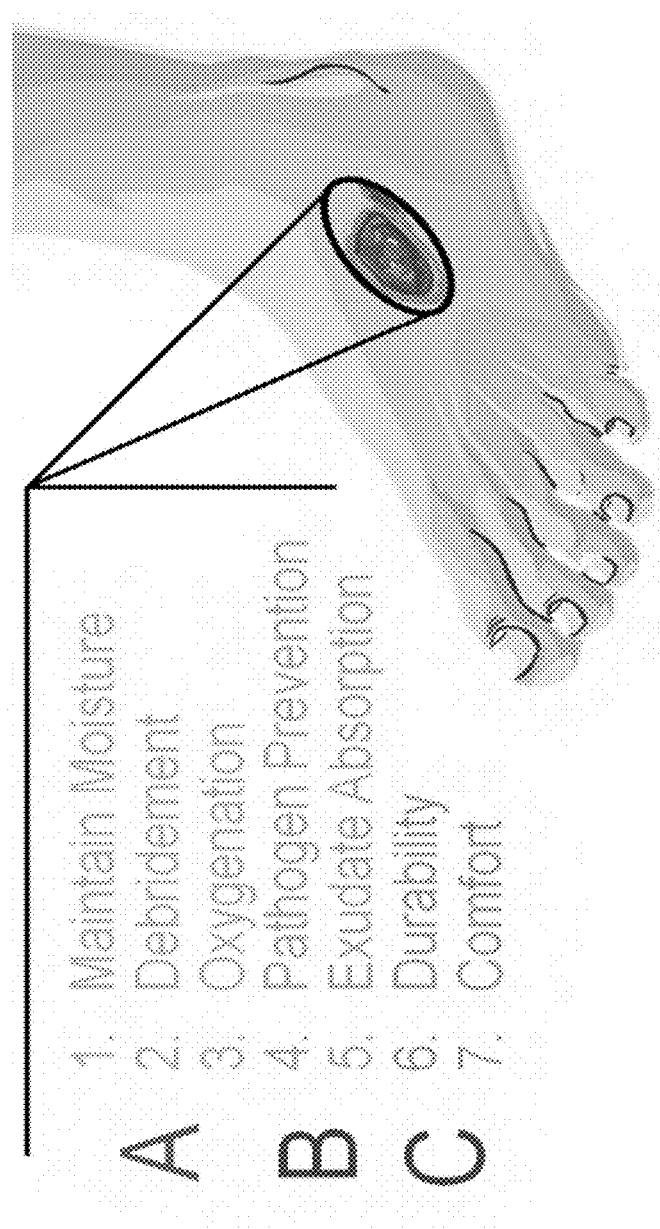
FIG. 8 is a diagram showing the so-called "ABCs" of chronic wound healing. The so-called ABCs as used herein are not a limiting aspect of this invention.

FIG. 8 is a diagram showing the so-called "ABCs" of chronic wound healing. The so-called ABCs as used herein are not a limiting aspect of this invention.

Figure 9:
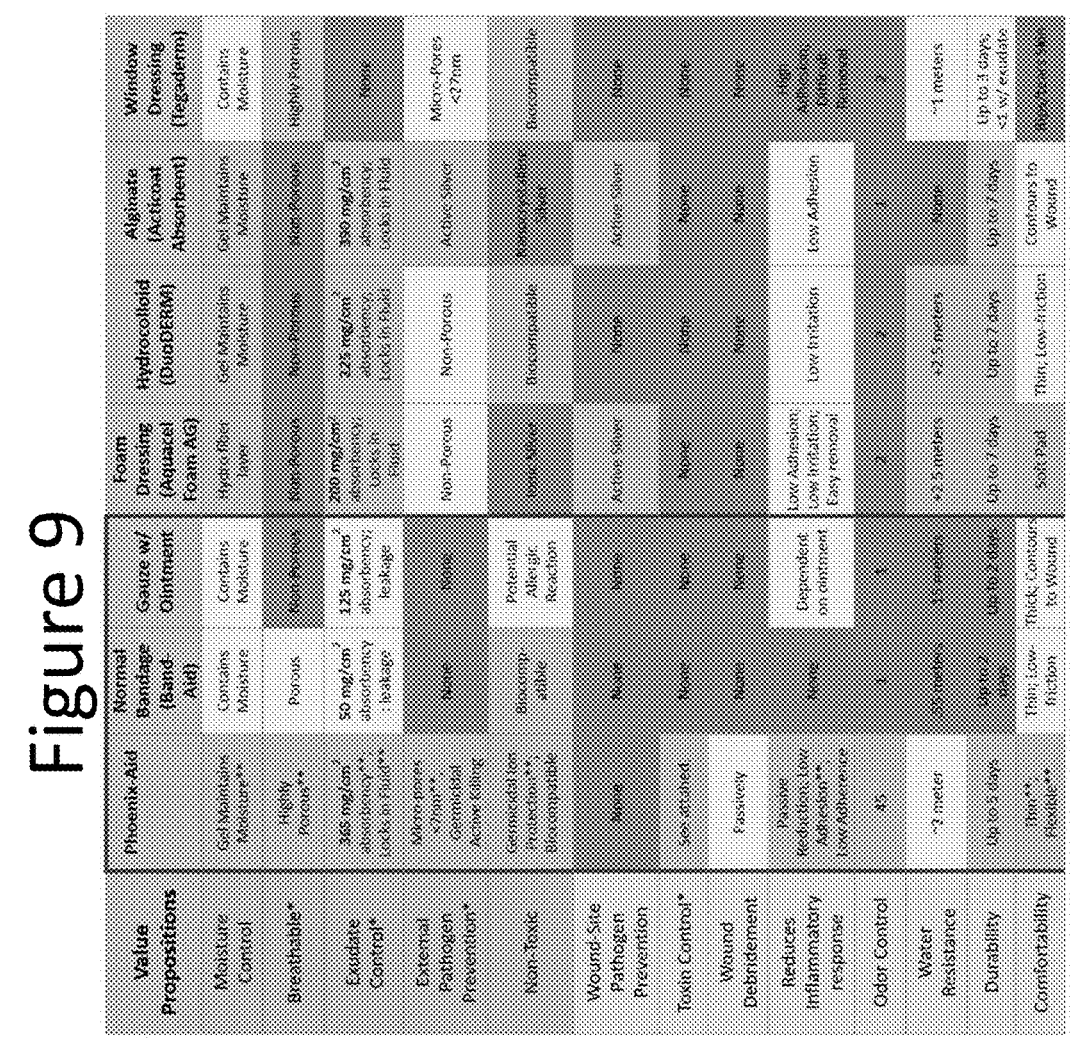

FIG. 9 is a diagram showing some results indicating that the invention is the preferred overall product across the metrics tested, although the invention is not limited by the metrics tested nor are the results indicative of all the various embodiments. In the figure, one embodiment of the invention taught herein is listed as "Phoenix-Aid."

FIG. 10 is a diagram showing retention results indicating breathability over time according to an embodiment of the current invention.

FIG. 11 is a diagram showing breathability testing where both the change and the R2 value were considered for a conclusion. A high change value and a linear (high R2 value) were desired for high breathability.

FIG. 12 is a diagram showing absorbency results place one embodiment of the invention (noted in the figure as "Phoenix-Aid") near the top of dressings tested.

FIG. 13 is a diagram showing liquid retained after applied force testing places on an embodiment of the current invention close to the top of products tested.

FIG. 14 is a diagram showing durability testing results.

FIG. 15 is a diagram showing waterproof testing results.

FIG. 16 is a diagram showing adhesion testing results.

Figure 17:
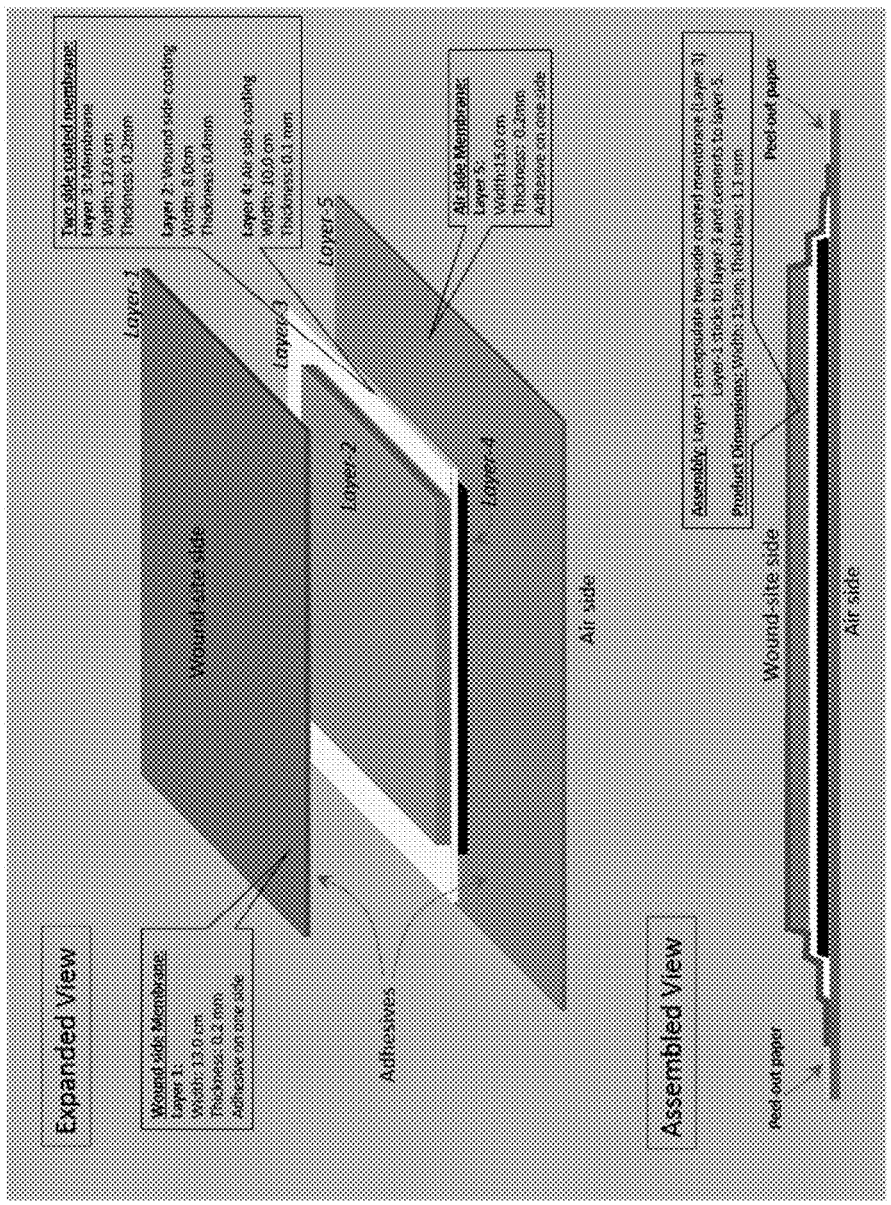
FIG. 17 is a diagram showing Specific Assembly Process.

FIG. 17 is a diagram showing an embodiment of an assembly process according to the current invention.

FIG. 18 is a chart showing test results of an embodiment of the invention taught herein; namely results of the absorption layer.

FIG. 19 is a chart showing test results of an embodiment of the invention taught herein; namely results of the seclusion layer.

Figure 20:
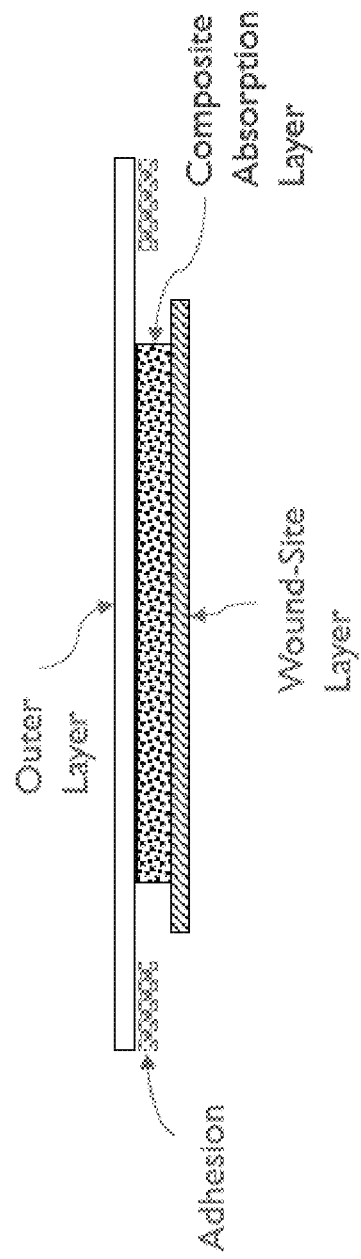
FIG. 20 is a schematic showing the side view of a 3-layer wound care dressing according to the present invention.

FIG. 20 is a schematic showing the side view of a 3-layer wound care dressing according to the present invention, including an outer layer, a composite absorption layer, and wound site layer. Potential sites for adhesives are also shown.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially" of any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

REFERENCES

All references are incorporated herein by reference.
1. Alexiadou K, Doupis J. Management of Diabetic Foot Ulcers. Diabetes Therapy. (2012); 3(1):4.

2. Centers for Disease Control and Prevention. National Diabetes Statistics Report: Estimates of Diabetes and Its Burden in the United States, 2014. Atlanta, Ga.: US Department of Health and Human Services; 2014.
3. De la Torre, Jorge & Chambers, J. (2011). Chronic wounds. Medscape.
4. Diabetic foot ulcers double death rate: Study. (2013). The Times of India.
5. Doughty, D., & McNichol, L. (2015). Wound, Ostomy and Continence Nurses Society® Core Curriculum: Wound Management. Lippincott Williams & Wilkins.
6. International Diabetes Federation. IDF Diabetes Atlas, 7 ed. (2015). Brussels, Belgium: International Diabetes Federation.
7. Johnson & Johnson. Sales of key products. (2014).
8. Lavery, L. A., Hunt, N. A., Ndip, A., Lavery, D. C., Van Houtum, W., & Boulton, A. J. (2010). Impact of chronic kidney disease on survival after amputation in individuals with diabetes.
Diabetes Care, 33(11), 2365-2369.
9. Narayan, Pushpa. 1 in 10 people in Tamil Nadu is diabetic. (2010). The Times of India.
10. Nix, D., Bryant, R. A., & Nix, D. P. (2012). Acute & Chronic Wounds: Current Management Concepts. Elsevier Mosby.
11. Patel, V., Chatterji, S., Chisholm, D., Ebrahim, S., Gopalakrishna, G., Mathers, C., . . . & Reddy, K. S. (2011). Chronic diseases and injuries in India. The Lancet, 377(9763), 413-428.
12. Margolis, D. J., Malay, D. S., Hoffstad, O. J., Leonard, C. E., MaCurdy, T., de Nava, K. L., . . . & Siegel, K. L. (2011). Incidence of diabetic foot ulcer and lower extremity amputation among Medicare beneficiaries, 2006 to 2008.
13. Sen, C. K., Gordillo, G. M., Roy, S., Kirsner, R., Lambert, L., Hunt, T. K., . . . & Longaker, M. T. (2009). Human skin wounds: a major and snowballing threat to public health and the economy. Wound Repair and Regeneration, 17(6), 763-771.
14. Shahi, S. K., Kumar, A., Kumar, S., & Singh, S. K. (2012). Prevalence of Diabetic Foot Ulcer and Associated Risk Factors in Diabetic Patients From North India. Age (years), 47(8.32), 55-26.
15. Stevens, P. The cost of diabetic foot ulcers. (2015).
16. Virginia Department of Health. Diabetes and prediabetes data. (2010). VDH.
17. Viswanathan, V., Kumpatla, S., Aravindalochanan, V., Rajan, R., Chinnasamy, C., Srinivasan, R., . . . & Kapur, A. (2012). Prevalence of diabetes and pre-diabetes and associated risk factors among tuberculosis patients in India. PloS one, 7(7), e41367.
18. Wound Educators. Wound dressings. (2016).
19. Euromonitor International. Wound care in India. (2016).

The invention claimed is:
1. A laminate for dressing wounds, comprising:
a macro-porous layer;
an absorption layer comprising carbon, absorbent material, and binding material, and wherein the absorption layer optionally further comprises germicidal ions; and
a wound-site layer, a micro-porous germicidal layer and an ion barrier layer, wherein the macro-porous layer is adjacent to the micro-porous germicidal layer; the micro-porous germicidal layer is adjacent to the ion-barrier layer; the ion-barrier layer is adjacent to the absorption layer; the absorption layer is adjacent to the wound-site layer; and the wound-site layer is adjacent to a wound during use of the laminate.

2. The laminate of claim 1, wherein:
the macroporous layer is configured to trap pathogens comprising pollen, mold spores, and fungal spores;
the micro-porous germicidal layer is configured to trap and kill pathogens comprising bacteria and viruses and comprises a size-exclusion barrier and germicidal ions;
the ion-barrier layer is configured to block the germicidal ions from the micro-porous germicidal layer;
the absorption later is configured to absorb and retain fluid; and
the wound-site layer is configured to maintain non-adherent contact with the wound during use of the laminate.

3. The laminate of claim 1, wherein the macroporous layer comprises a woven or unwoven mesoporous or macroporous membrane comprising one or more of HEPA (high-efficiency particulate air filter) membrane, ULPA (ultra-low penetration air filter) membrane, micro-cellulose, polyester, polypropylene, nylon, microfiber, viscose, cotton fabric tape, polypropylene textile fabric cloth, perforated silicone, and/or porous silicone.

4. The laminate of claim 1, wherein the macroporous layer has a pore size in the range of 6-500 nm in diameter.

5. The laminate of claim 1, wherein the micro-porous germicidal layer comprises carbon or a polymer carbon composite comprising carbon, germicidal ions, and/or binding material.

6. The laminate of claim 1, wherein the micro-porous germicidal layer has a pore size of less than 5 nm in diameter.

7. The laminate of claim 1, wherein the micro-porous germicidal layer has pores which contain germicidal ions.

8. The laminate of claim 5, wherein the germicidal ions are impregnated in the micro-porous germicidal layer at a concentration of 2 to 1000 parts per million.

9. The laminate of claim 5, wherein the carbon comprises one or more of activated carbon, powdered activated carbon, activated carbon blended with graphene, activated carbon blended with nano-graphite powdered form, and/or any combination thereof.

10. The laminate of claim 5, wherein the germicidal ions comprise one or more of silver nitrate, nano-ionic silver, ionic silver, colloidal silver, ionic copper, colloidal copper, ionic arsenic, colloidal arsenic, ionic mercury, colloidal mercury, and/or any combination thereof.

11. The laminate of claim 5, wherein the binding material comprises one or more of silicone, polyvinylidene fluoride, polyvinyl chloride, and/or combination thereof.

12. The laminate of claim 1, wherein the ion-barrier layer comprises one or more of a HEPA (high-efficiency particulate air filter) membrane, ULPA (ultra-low penetration air filter) membrane, an unwoven or woven cotton, polyester, polypropylene, nylon, micro-cellulose, viscose, polypropylene textile fabric cloth, porous silicone, perforated silicone membrane, and/or any combination thereof.

13. The laminate of claim 1, wherein the absorption layer comprises carbon or a polymer-carbon composite comprising carbon, germicidal ions, absorbent material, and/or binding material.

14. The laminate of claim 1, wherein the absorption layer has pores which contain germicidal ions.

15. The laminate of claim 13, wherein the germicidal ions are impregnated in the absorption layer at a concentration of 2 to 1000 parts per million.

16. The laminate of claim 13, wherein the carbon comprises one or more of activated carbon, powdered activated carbon, activated carbon blended with graphene, activated carbon blended with nano-graphite powdered form, and/or any combination thereof.

17. The laminate of claim 13, wherein the germicidal ions comprise one or more of silver nitrate, nano-ionic silver, ionic silver, colloidal silver, ionic copper, colloidal copper, ionic arsenic, colloidal arsenic, ionic mercury, colloidal mercury, and/or any combination thereof.

18. The laminate of claim 13, wherein the absorbent material comprises one or more polymer comprising sodium polyacrylate, polyacrylamide copolymer, cellulose, and/or any combination thereof.

19. The laminate of claim 13, wherein the binding material comprises one or more of silicone, polyvinylidene fluoride, polyvinyl chloride, and/or any combination thereof.

20. The laminate of claim 1, wherein the wound-site layer comprises a woven or unwoven, mesoporous, or macroporous membrane comprising one or more of HEPA (high-efficiency particulate air filter) membrane, ULPA (ultra-low penetration air filter) membrane, a combination of both HEPA and ULPA, unwoven or woven cotton, polyester, nylon, viscose or polypropylene textile fabric cloth, perforated silicone, porous silicone, and/or any combination thereof.

21. The laminate of claim 1, wherein the wound-site layer is coated with one or more of a layer of activated carbon, water resistant material, and/or adhesive.

22. The laminate of claim 1, wherein the macro-porous layer is coated with a water resistant material and/or adhesive.

23. A bandage, diaper, sanitary pad, tampon, or pad comprising the laminate of claim 1.

* * * * *